United States Patent
Aoyama et al.

(10) Patent No.: US 10,986,987 B2
(45) Date of Patent: Apr. 27, 2021

(54) PROCESSOR DEVICE AND ENDOSCOPE SYSTEM

(71) Applicant: FUJIFILM Corporation, Tokyo (JP)

(72) Inventors: Tatsuya Aoyama, Kanagawa (JP); Hiroaki Yamamoto, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 117 days.

(21) Appl. No.: 16/395,262

(22) Filed: Apr. 26, 2019

(65) Prior Publication Data
US 2019/0254509 A1  Aug. 22, 2019

Related U.S. Application Data

(63) Continuation of application No. PCT/JP2017/035877, filed on Oct. 2, 2017.

(30) Foreign Application Priority Data

Oct. 27, 2016  (JP) .............................. JP2016-211060

(51) Int. Cl.
*G06K 9/00* (2006.01)
*A61B 1/045* (2006.01)
(Continued)

(52) U.S. Cl.
CPC .......... *A61B 1/045* (2013.01); *A61B 1/00006* (2013.01); *A61B 1/00009* (2013.01);
(Continued)

(58) Field of Classification Search
None
See application file for complete search history.

(56) References Cited

U.S. PATENT DOCUMENTS 8,994,801 B2  3/2015  Tanaka et al.
2004/0059215 A1*  3/2004  Nishimura ............. G16H 15/00
                                                            600/410
(Continued)

FOREIGN PATENT DOCUMENTS

EP  3520676  8/2019
EP  3524132  8/2019
(Continued)

OTHER PUBLICATIONS

"Office Action of Japan Counterpart Application", dated May 26, 2020, with English translation, p. 1-p. 10.
(Continued)

*Primary Examiner* — Wei Wen Yang
(74) *Attorney, Agent, or Firm* — JCIPRNET

(57) ABSTRACT

A processor device and an endoscope system capable of calculating an optimal index value in accordance with a diagnosis purpose is provided. A processor device includes an image acquisition unit, a diagnosis purpose acquisition unit, an index value storage unit, an index value selection unit, and an index value calculation unit. The image acquisition unit acquires an endoscope image obtained by an endoscope image-capturing an observation object. The diagnosis purpose acquisition unit acquires a diagnosis purpose. The index value storage unit stores correspondence between the diagnosis purpose and a plurality of index values relating to a structure of the observation object. The index value selection unit refers to the index value storage unit and selects the index value that is used for the acquired diagnosis purpose. The index value calculation unit uses the endoscope image and calculates the selected index value.

20 Claims, 17 Drawing Sheets

(51) Int. Cl.
    *A61B 1/00*     (2006.01)
    *A61B 1/04*     (2006.01)
    *A61B 1/06*     (2006.01)
    *H04N 5/225*     (2006.01)
    *G06T 7/00*     (2017.01)

(52) U.S. Cl.
    CPC .......... *A61B 1/00039* (2013.01); *A61B 1/042* (2013.01); *A61B 1/06* (2013.01); *A61B 1/0638* (2013.01); *H04N 5/2256* (2013.01); *G06T 7/0012* (2013.01); *H04N 2005/2255* (2013.01)

(56) References Cited

U.S. PATENT DOCUMENTS

| | | | |
|---|---|---|---|
| 2011/0075900 A1* | 3/2011 | Masumoto | G16H 50/20 382/128 |
| 2011/0242301 A1 | 10/2011 | Morita | |
| 2012/0190922 A1 | 7/2012 | Kaku | |
| 2012/0327205 A1 | 12/2012 | Takahashi | |
| 2013/0131465 A1 | 5/2013 | Yamamoto et al. | |
| 2018/0114319 A1* | 4/2018 | Kono | A61B 1/126 |

FOREIGN PATENT DOCUMENTS

| | | |
|---|---|---|
| JP | 2002177214 | 6/2002 |
| JP | 2002336193 | 11/2002 |
| JP | 2003126045 | 5/2003 |
| JP | 2011135983 | 7/2011 |
| JP | 2011206251 | 10/2011 |
| JP | 2012045373 | 3/2012 |
| JP | 2012152279 | 8/2012 |
| JP | 2016015995 | 2/2016 |
| JP | 2016067706 | 5/2016 |
| JP | 2016087370 | 5/2016 |
| WO | 2013140667 | 9/2013 |

OTHER PUBLICATIONS

"Search Report of Europe Counterpart Application", dated Oct. 16, 2019, p. 1-p. 8.

"International Search Report (Form PCT/ISA/210) of PCT/JP2017/035877," dated Dec. 5, 2017, with English translation thereof, pp. 1-5.

"International Preliminary Report on Patentability (Form PCT/IPEA/409) of PCT/JP2017/035877," completed on Nov. 13, 2018, with English translation thereof, pp. 1-13.

* cited by examiner

FIG. 6

104 INDEX VALUE STORAGE UNIT

104a

| FIRST DIAGNOSIS PURPOSE | INDEX VALUE |
|---|---|
| LARGE INTESTINE SCREENING | COMPLEXITY OF SURFACE LAYER BLOOD VESSEL |
| | COMPLEXITY OF MIDDLE LAYER BLOOD VESSEL |
| STOMACH SCREENING | COMPLEXITY OF MIDDLE LAYER BLOOD VESSEL |
| | UNIFORMITY OF SURFACE STRUCTURE |
| LARGE INTESTINE CLOSE INSPECTION | DENSITY OF SURFACE LAYER BLOOD VESSEL |

104b

| SECOND DIAGNOSIS PURPOSE | INDEX VALUE |
|---|---|
| BARRETT'S ESOPHAGUS | DENSITY OF SURFACE LAYER BLOOD VESSEL |
| | COMPLEXITY OF SURFACE LAYER BLOOD VESSEL |
| | DENSITY OF MIDDLE LAYER BLOOD VESSEL |
| | COMPLEXITY OF MIDDLE LAYER BLOOD VESSEL |
| LARGE INTESTINAL POLYPOSIS | UNIFORMITY OF THICKNESS OF MIDDLE LAYER BLOOD VESSEL |
| | UNIFORMITY OF SURFACE STRUCTURE |
| ANGIODYSPLASIA | DENSITY OF MIDDLE LAYER BLOOD VESSEL |

104c

| THIRD DIAGNOSIS PURPOSE | INDEX VALUE |
|---|---|
| REMISSION PERIOD OF ULCERATIVE COLITIS | COMPLEXITY OF SURFACE LAYER BLOOD VESSEL |
| | COMPLEXITY OF MIDDLE LAYER BLOOD VESSEL |
| ACTIVE PERIOD OF ULCERATIVE COLITIS | COMPLEXITY OF SURFACE LAYER BLOOD VESSEL |

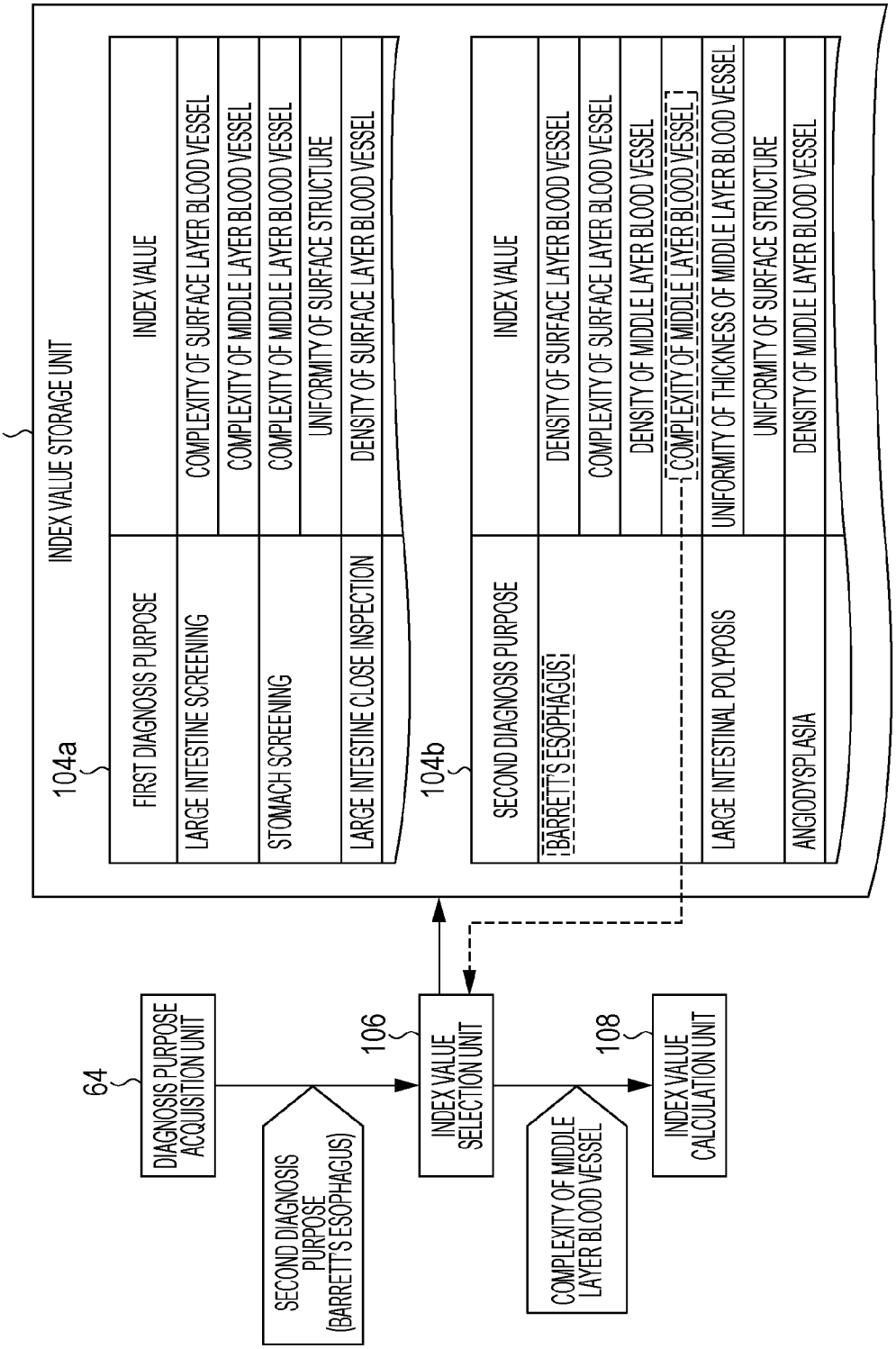

FIG. 13

122 INDEX VALUE STORAGE UNIT

122a

| FIRST DIAGNOSIS PURPOSE | INDEX VALUE | COEFFICIENT |
|---|---|---|
| LARGE INTESTINE SCREENING | COMPLEXITY OF SURFACE LAYER BLOOD VESSEL | 0.5 |
| | COMPLEXITY OF MIDDLE LAYER BLOOD VESSEL | 1 |
| STOMACH SCREENING | COMPLEXITY OF MIDDLE LAYER BLOOD VESSEL | 1 |
| | UNIFORMITY OF SURFACE STRUCTURE | 1 |
| LARGE INTESTINE CLOSE INSPECTION | DENSITY OF SURFACE LAYER BLOOD VESSEL | 1 |

122b

| SECOND DIAGNOSIS PURPOSE | INDEX VALUE | COEFFICIENT |
|---|---|---|
| BARRETT'S ESOPHAGUS | DENSITY OF SURFACE LAYER BLOOD VESSEL | 1 |
| | COMPLEXITY OF SURFACE LAYER BLOOD VESSEL | 1 |
| | DENSITY OF MIDDLE LAYER BLOOD VESSEL | 1 |
| | COMPLEXITY OF MIDDLE LAYER BLOOD VESSEL | 1 |
| LARGE INTESTINAL POLYPOSIS | UNIFORMITY OF THICKNESS OF MIDDLE LAYER BLOOD VESSEL | 1 |
| | UNIFORMITY OF SURFACE STRUCTURE | 0.5 |
| ANGIODYSPLASIA | DENSITY OF MIDDLE LAYER BLOOD VESSEL | 1 |

122c

| THIRD DIAGNOSIS PURPOSE | INDEX VALUE | COEFFICIENT |
|---|---|---|
| REMISSION PERIOD OF ULCERATIVE COLITIS | COMPLEXITY OF SURFACE LAYER BLOOD VESSEL | 1 |
| | COMPLEXITY OF MIDDLE LAYER BLOOD VESSEL | 1 |
| ACTIVE PERIOD OF ULCERATIVE COLITIS | COMPLEXITY OF SURFACE LAYER BLOOD VESSEL | 1 |

PROCESSOR DEVICE AND ENDOSCOPE SYSTEM

CROSS REFERENCE TO RELATED APPLICATIONS

This application is a Continuation of PCT International Application No. PCT/JP2017/035877 filed on Oct. 2, 2017, which claims priority under 35 U.S.C § 119(a) to Patent Application No. 2016-211060 filed in Japan on Oct. 27, 2016, all of which are hereby expressly incorporated by reference into the present application.

BACKGROUND OF THE INVENTION

1. Field of the Invention

The present invention relates to a processor device and an endoscope system.

2. Description of the Related Art

In medical fields, diagnoses using an endoscope system including a light source device, an endoscope, and a processor device are being widely performed. With an endoscope system, an observation object is irradiated with illumination light emitted by a light source device via an endoscope, an image signal is obtained by image-capturing the observation object illuminated with the illumination light, and a processor device generates an image of the observation object on the basis of the image signal. By displaying the image on a monitor, a doctor can make a diagnosis while watching the image on the monitor.

Moreover, in endoscopic diagnoses in recent years, as described in JP2016-087370A, a diagnosis assisting system is being introduced to fill a difference in skill among doctors. The diagnosis assisting system extracts a feature of a lesion portion from an image obtained by imaging an observation object, indexes the feature, and displays the index. Furthermore, as described in JP2002-177214A, a search system is being introduced that can efficiently search for cases of disease similar to the current diagnosis purpose by additionally registering an extracted feature as search information when an image is filed.

SUMMARY OF THE INVENTION

Endoscopic diagnoses handle various subject diseases, diagnosis purposes, and stages of diseases to be inspected. Hence it is required to calculate an index value optimal for a diagnosis purpose of such subject diseases and so forth and to provide the index value to a user. Regarding this, JP2016-087370A and JP2002-177214A do not describe or suggest a technical feature in the viewpoint of calculating an index value optimal for a diagnosis purpose.

Therefore, an endoscope system like JP2016-087370A is being requested to set an index value to be focused optimal for a diagnosis purpose, the optimal index value which allows a portion that seems to be abnormal to be detected without omission like screening, and to provide the optimal index value to a user in an easily viewable manner. Furthermore, a search system like JP2002-177214A is being requested to further increase the efficiency of search by providing, as accessory information, an optimal index value corresponding to a diagnosis purpose.

An object of the present invention is to provide a processor device and an endoscope system capable of calculating an optimal index value in accordance with a diagnosis purpose.

A processor device according to the present invention includes an image acquisition unit that acquires an endoscope image obtained by an endoscope image-capturing an observation object; a diagnosis purpose acquisition unit that acquires a diagnosis purpose; an index value storage unit that stores correspondence between the diagnosis purpose and a plurality of index values relating to a structure of the observation object; an index value selection unit that refers to the index value storage unit and selects an index value that is used for the acquired diagnosis purpose; and an index value calculation unit that uses the endoscope image and calculates the selected index value.

Preferably, the diagnosis purpose includes a first diagnosis purpose including screening and close inspection, a second diagnosis purpose relating to a type of disease, and a third diagnosis purpose relating to a stage of disease; and the index value selection unit selects the index value in accordance with one diagnosis purpose of the first to third diagnosis purposes.

Preferably, the processor device further includes a first emphasis image generation unit that uses the endoscope image and the calculated index value, and generates a first emphasis image in which the structure is emphasized.

Preferably, the processor device further includes a first image storage unit that stores the first emphasis image in association with at least one of the acquired diagnosis purpose or the calculated index value.

Preferably, the processor device further includes a structure parameter calculation unit that calculates a structure parameter of the structure by weighting a plurality of the index values with a weighting coefficient determined in accordance with the diagnosis purpose and arithmetically operating the index values.

Preferably, the processor device further includes a second emphasis image generation unit that uses the endoscope image and the calculated structure parameter, and generates a second emphasis image in which the structure is emphasized.

Preferably, the processor device further includes a second image storage unit that stores the second emphasis image in association with at least one of the acquired diagnosis purpose or the calculated structure parameter.

Preferably, the processor device further includes a determination unit that uses the structure parameter and determines a state of a mucous membrane of the observation object.

Preferably, the processor device further includes a third emphasis image generation unit that uses the endoscope image and a result of the determination, and generates a third emphasis image in which the structure is emphasized.

Preferably, the processor device further includes a third image storage unit that stores the third emphasis image in association with at least one of the acquired diagnosis purpose or the result of the determination.

Preferably, the processor device is connected to an endoscope information management system having a data storage unit that stores endoscope information management data including the diagnosis purpose so as to mutually communicate with each other through a network; and the diagnosis purpose acquisition unit receives the endoscope information management data through the network, and acquires the diagnosis purpose by extracting the diagnosis purpose from the received endoscope information management data.

The processor device may further include a diagnosis purpose input unit that inputs the diagnosis purpose, and the diagnosis purpose acquisition unit may acquire the diagnosis purpose input by the diagnosis purpose input unit.

An endoscope system according to the present invention includes a light source that emits illumination light; an image acquisition unit that acquires an endoscope image acquired by an endoscope image-capturing an observation object illuminated with the illumination light; a structure extraction unit that uses the endoscope image and generates a structure extraction image obtained by extracting a structure of the observation object; a diagnosis purpose acquisition unit that acquires a diagnosis purpose; an index value storage unit that stores correspondence between the diagnosis purpose and a plurality of index values relating to a structure of the observation object; an index value selection unit that refers to the index value storage unit and selects an index value that is used for the acquired diagnosis purpose; an index value calculation unit that uses the structure extraction image and calculates the selected index value; a first emphasis image generation unit that uses the endoscope image and the calculated index value, and generates a first emphasis image in which the structure is emphasized; and a display unit that displays the first emphasis image.

With the processor device and the endoscope system of the present invention, the optimal index value can be calculated in accordance with the diagnosis purpose.

BRIEF DESCRIPTION OF THE DRAWINGS

FIG. 6 is an illustration explaining an index value storage unit;

FIG. 7 is an illustration explaining an index value selection unit;

FIG. 13 is an illustration explaining an index value storage unit according to the second embodiment;

DESCRIPTION OF THE PREFERRED EMBODIMENTS

First Embodiment

Figure 1:
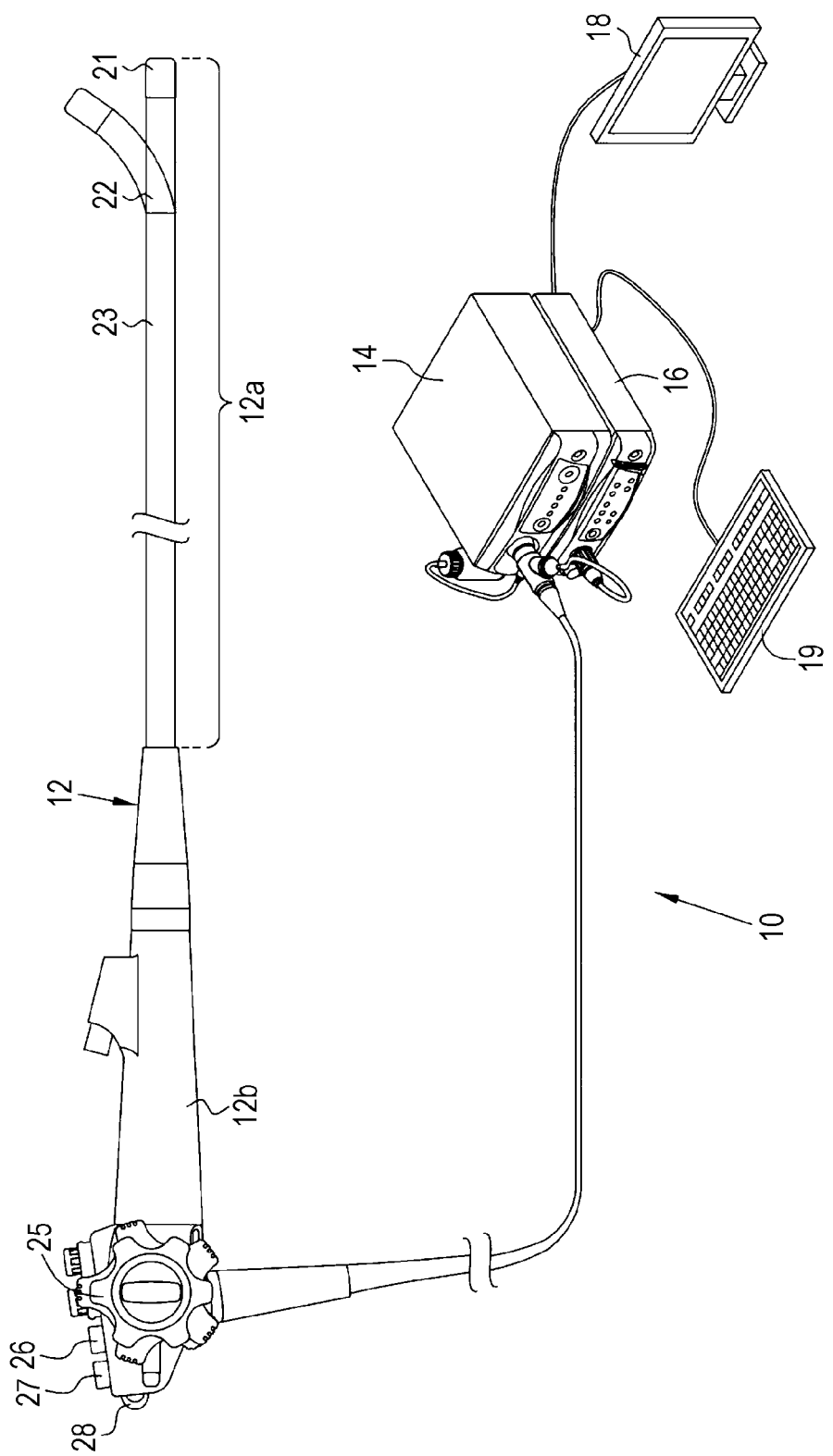
FIG. 1 is an external view of an endoscope system according to a first embodiment.

As illustrated in FIG. 1, an endoscope system 10 has an endoscope 12, a light source device 14, a processor device 16, a display unit 18, and an instruction input part 19. The endoscope 12 image-captures an observation portion in a living body serving as a subject. The light source device 14 supplies illumination light that illuminates the observation portion, to the endoscope 12. The processor device 16 generates a display image of the observation portion by using an image pick-up signal obtained by image-capturing. The display unit 18 is a monitor that displays a display image and information and so forth accompanying the display image. The instruction input part 19 is a console of a keyboard, a mouse, and so forth, and functions as a user interface that receives input operations, such as designation of a region of interest (ROI) and functional setting. The display unit 18 and the instruction input part 19 are electrically connected to the processor device 16.

The endoscope 12 is optically connected to the light source device 14, and is electrically connected to the processor device 16. The endoscope 12 has an insertion section 12a and an operation section 12b.

The insertion section 12a is a section that is inserted into an alimentary canal or the like of the living body. The insertion section 12a has a distal end portion 21, a bending portion 22, and a flexible pipe portion 23 that are coupled in that order from the distal end side. The distal end portion 21 has, at a distal end surface, an illumination window, an observation window, an air/water supply nozzle, and a forceps port (none of these is illustrated). The illumination window is for irradiating the observation portion with the illumination light. The observation window is for taking in the light from the observation portion. The air/water supply nozzle is for washing the illumination window and the observation window. The forceps port is for performing various treatments using treatment tools, such as a pair of forceps and an electric scalpel. The bending portion 22 is constituted by coupling a plurality of bending pieces, and bends in up-down and left-right directions. The flexible pipe portion 23 is flexible, and can be inserted into a bending tubular path, such as the esophagus or intestine.

The operation section 12b has an angle knob 25, an image storage operating unit 26, a mode switching unit 27, and a zoom operating unit 28. The angle knob 25 is used for an operation of bending the bending portion 22 so as to direct the distal end portion 21 in a desirable direction. The image storage operating unit 26 is used for an operation of storing a still image and/or a movie in a storage (not illustrated). The mode switching unit 27 is used for an operation of switching an observation mode. The zoom operating unit 28 is used for an operation of changing zoom magnification.

The endoscope system 10 has, as operation modes, a normal observation mode, a special observation mode, and a suitable object observation mode. In the normal observation mode, an image in which an observation object with natural colors is captured (hereinafter, referred to as normal observation image) is acquired. In the special observation mode, an image in which a blood vessel that is an observation object is at least emphasized (hereinafter, referred to as special observation image) is acquired. In the suitable object observation mode, an image in which a structure that is an observation object suitable for the diagnosis purpose is emphasized (hereinafter, referred to as suitable object observation image) is acquired. In this embodiment, a structure includes a structure of a blood vessel and a structure of a gland duct (pit pattern). In the following description, when a structure of a blood vessel and a structure of a gland duct are not distinguished from each other, these structures each are referred to as a structure.

Figure 2:
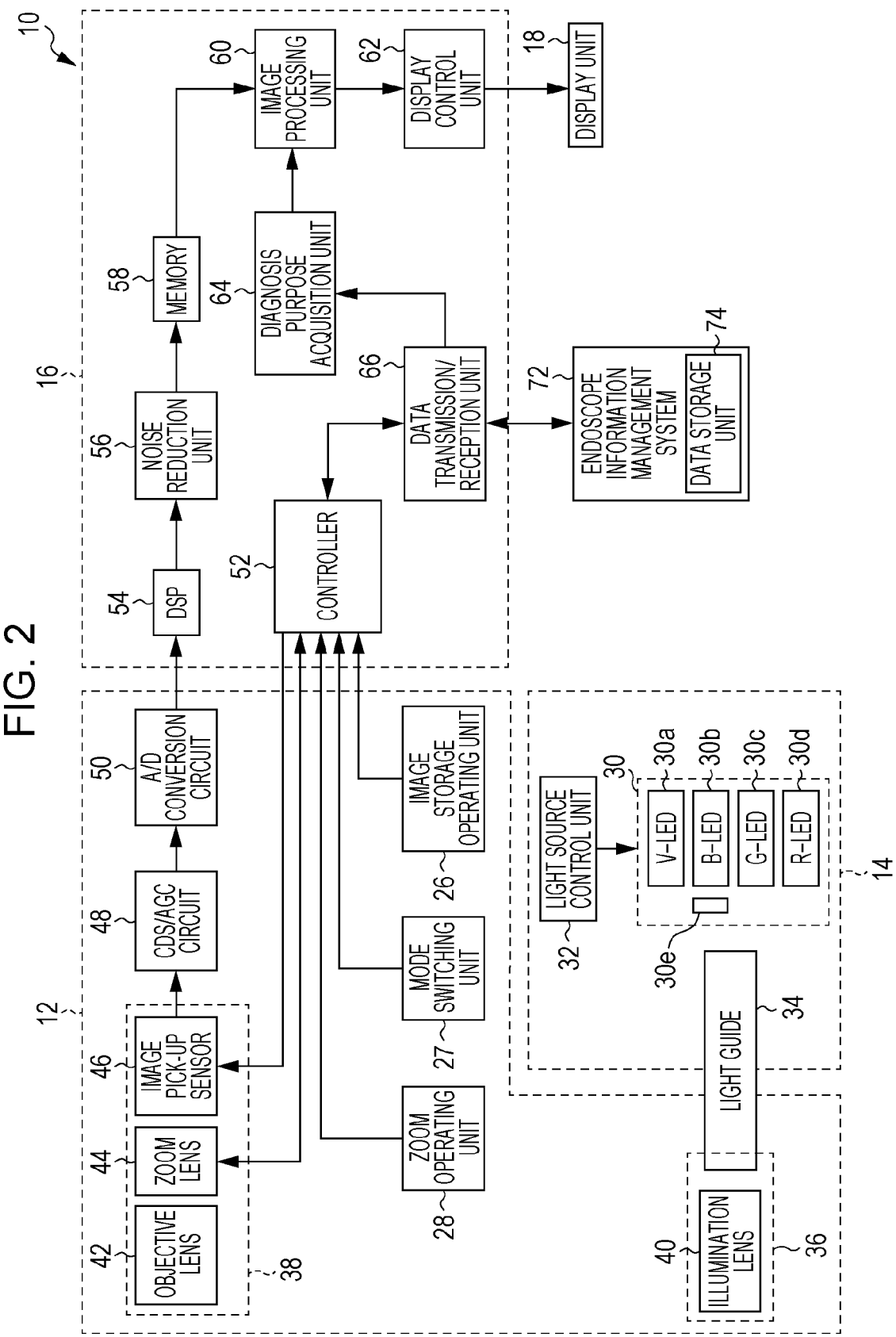
FIG. 2 is a block diagram illustrating a function of the endoscope system.

As illustrated in FIG. 2, the light source device 14 includes a light source 30 that emits illumination light, and a light source control unit 32 that controls the light source 30. The light source 30 is, for example, a semiconductor light source such as light emitting diodes (LEDs) of a plurality of colors with different wavelength ranges.

In this embodiment, the light source 30 has, for example, four-color LEDs of a violet light emitting diode (V-LED) 30a, a blue light emitting diode (B-LED) 30b, a green light emitting diode (G-LED) 30c, and a red light emitting diode (R-LED) 30d. The V-LED 30a emits light with light emission wavelengths in a range of from 380 nm to 420 nm. The B-LED 30b emits light with light emission wavelengths in a range of from 420 nm to 500 nm. The G-LED 30c emits light with light emission wavelengths in a range of from 480 nm to 600 nm. The R-LED 30d emits light with light emission wavelengths in a range of from 600 nm to 650 nm. The lights of the respective colors may each have the same central wavelength and peak wavelength, or may have different central wavelength and peak wavelength.

The light source 30 includes an optical filter 30e that adjusts the wavelength range of light emitted from a LED. In this embodiment, the optical filter 30e is arranged on the optical path of the B-LED 30b, and transmits a short wavelength component included in the wavelength range of the B-LED 30b. To be specific, the optical filter 30e transmits light of 450 nm or shorter included in the wavelength range of the B-LED 30b. A long wavelength component included in the wavelength range of the B-LED 30b decreases the contrast between a mucous membrane and a blood vessel. Thus, by using the optical filter 30e, the short wavelength component included in the wavelength range of the B-LED 30b is supplied to a light guide 34 (described later). The optical filter 30e is arranged on the optical path of the B-LED 30b in this embodiment; however, it is not limited thereto. For example, the optical filter 30e may be arranged on the optical path of the G-LED 30c. The wavelength component to be transmitted by the optical filter 30e can be appropriately set. For example, when the optical filter 30e is arranged on the optical path of the G-LED 30c, the optical filter 30e transmits part of the wavelength range of the G-LED 30c.

The light source control unit 32 adjusts the light emitting timing, light emitting duration, light quantity, and spectrum of illumination light of each of the LEDs 30a to 30d by independently controlling turning ON or OFF of each of the LEDs 30a to 30d, and the balance of respective emission light quantities of the LEDs 30a to 30d (hereinafter, referred to as light quantity ratio). In this embodiment, the light source control unit 32 controls the light quantity ratio of the LEDs 30a to 30d on an observation mode basis by adjusting the electric current and voltage for driving each of the LEDs 30a to 30d.

Figure 3:
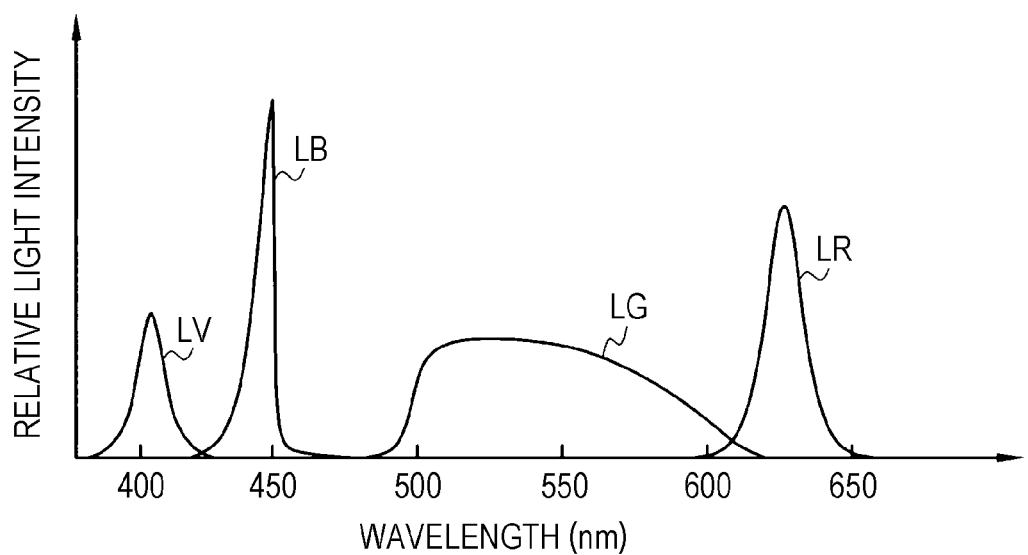
FIG. 3 illustrates a light intensity spectrum of illumination light in a normal observation mode.

As illustrated in FIG. 3, in the normal observation mode, the light source control unit 32 turns ON all the LEDs 30a to 30d, and hence almost white illumination light (hereinafter, referred to as white light) including violet light LV emitted from the V-LED 30a, blue light LB emitted from the B-LED 30b, green light LG emitted from the G-LED 30c, and red light LR emitted from the R-LED 30d is emitted. In this embodiment, the blue light LB is light transmitted through the optical filter 30e, that is, light of 450 nm or shorter included in the wavelength range of the B-LED 30b. The violet light LV is light in a wavelength range that is optimal for observing a surface layer blood vessel located at a shallow position from a mucous membrane surface. The blue light LB is light in a wavelength range that is optimal for observing a middle layer blood vessel located at a position deeper than the position of a surface layer blood vessel.

Figure 4:
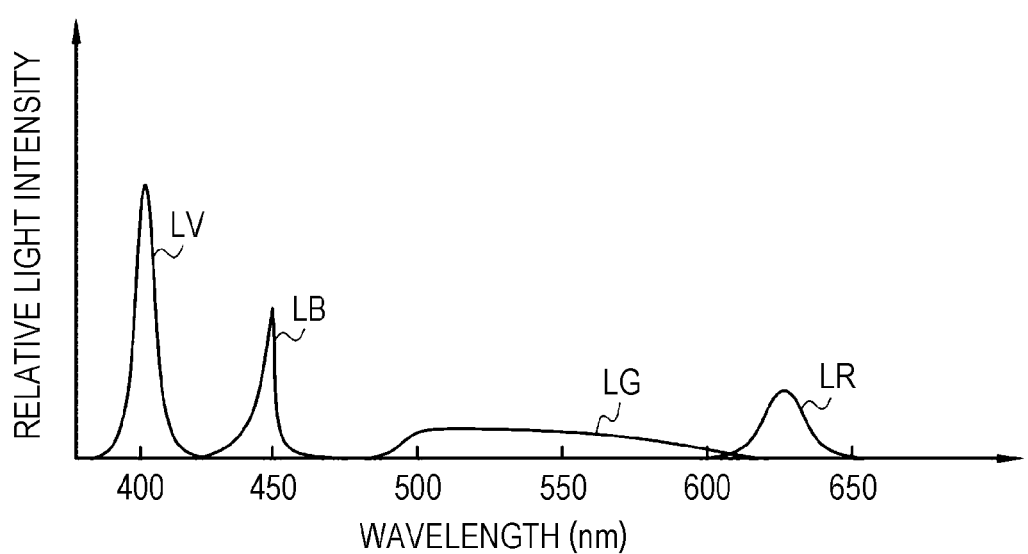
FIG. 4 illustrates a light intensity spectrum of illumination light in a special observation mode.

As illustrated in FIG. 4, in the special observation mode, the light source control unit 32 causes illumination light to be emitted such that the emission light quantity of the V-LED 30a is larger than that in the normal observation mode and the respective emission light quantities of the B-LED 30b, G-LED 30c, and R-LED 30d are smaller than those in the normal observation mode.

In the case of the suitable object observation mode, the light source control unit 32 controls to turn ON each LED so as to emit previously set illumination light. The illumination light to be emitted is set through, for example, an input operation with the instruction input part 19. In this embodiment, the light source control unit 32 controls to turn ON the V-LED 30a and the B-LED 30b from among the respective LEDs 30a to 30d. Hence, in the suitable object observation mode, illumination light including the violet light LV and the blue light LB is emitted. The light source control unit 32 may sequentially emit the violet light LV and the blue light LB by switching between control that turns ON only the V-LED 30a and control that turns ON only the B-LED 30b. Further, the illumination light in the suitable object observation mode is not limited to the illumination light including the violet light LV and the blue light LB. For example, illumination light consisting of only green light LG, illumination light consisting of only red light LR, illumination light including the violet light LV and the red light LR, illumination light including the blue light LB and the red light LR, and so forth, may be appropriately set.

The illumination light emitted from the light source 30 is incident on the light guide 34 inserted through the insertion section 12a. The light guide 34 is embedded in the endoscope 12 and a universal cord. Illumination light propagates through the light guide 34 to the distal end portion 21 of the endoscope 12. The universal cord is a cord that connects the endoscope 12, the light source device 14, and the processor device 16 to one another. For the light guide 34, a multimode fiber can be used. For example, for the light guide 34, a small-diameter fiber cable having a core diameter of 105 μm, a cladding diameter of 125 μm, and a diameter including a protective layer serving as an outer cover in a range of from ϕ0.3 to 0.5 mm can be used.

The distal end portion 21 has an illumination optical system 36 and an image pick-up optical system 38. The illumination optical system 36 has an illumination lens 40. The illumination light propagating through the light guide 34 illuminates an observation object via the illumination lens 40. The image pick-up optical system 38 has an objective lens 42, a zoom lens 44, and an image pick-up sensor 46. Various lights, such as reflected light, scattered light, and fluorescence, from the observation object are incident on the image pick-up sensor 46 via the objective lens 42 and the zoom lens 44. Thus, an image of the observation object is formed on the image pick-up sensor 46. The zoom lens 44 freely moves between the telephoto end and the wide end by operating the zoom operating unit 28, to enlarge or contract the image of the observation object formed on the image pick-up sensor 46.

The image pick-up sensor 46 is a color image pick-up sensor provided with a color filter of one of primary colors of red (R), green (G), and blue (B) for each pixel, image-captures the observation object, and outputs an image signal of corresponding one of RGB. For the image pick-up sensor 46, a charge coupled device (CCD) image pick-up sensor, a complementary metal-oxide semiconductor (CMOS) image pick-up sensor, or the like, can be used. Alternatively, instead of the image pick-up sensor 46 provided with the color filters of the primary colors, a complementary-color image pick-up sensor including complementary-color filters of cyan (C), magenta (M), yellow (Y), and green (G) may be used. When the complementary-color image pick-up sensor is used, image signals of four colors of CMYG are output. By converting the image signals of the four colors of CMYG into the image signals of the three colors of RGB by color conversion from complementary colors to primary colors, image signals of the respective colors of RGB similar to those of the image pick-up sensor 46 can be obtained. Instead of the image pick-up sensor 46, a monochrome sensor without a color filter may be used.

A correlated double sampling (CDS)/automatic gain control (AGC) circuit 48 performs correlative double sampling and automatic gain control on an analog image signal output from the image pick-up sensor 46. An analog to digital (A/D) conversion circuit 50 converts the analog image signal output from the CDS/AGC circuit 48 into a digital image signal. The A/D conversion circuit 50 inputs the digital image signal after the A/D conversion to the processor device 16.

The processor device 16 includes a controller 52, a digital signal processor (DSP) 54, a noise reduction unit 56, a memory 58, an image processing unit 60, a display control unit 62, a diagnosis purpose acquisition unit 64, and a data transmission/reception unit 66.

The controller 52 has a central processing unit (CPU), a read only memory (ROM) that stores a control program and setting data required for the control, and a random access memory (RAM) serving as a work memory that loads the control program. When the CPU executes the control program, the controller 52 controls respective units of the processor device 16. The respective units of the processor device 16 each may be composed of a programmable logic device (PLD) that is a processor whose circuit configuration is changeable after manufacturing, such as a field programmable gate array (FPGA); or a dedicated electric circuit having a circuit configuration designed dedicatedly for executing specific processing, such as an application specific integrated circuit (ASIC). The above configuration can be similarly applied to the inside portions of the endoscope 12 and the light source device 14.

The DSP 54 acquires the digital image signal from the endoscope 12, and performs various signal processing on the acquired image signal, for example, defect correction processing, offset processing, gain correction processing, linear matrix processing, gamma conversion processing, and demosaicing processing. The defect correction processing corrects a signal of a defect pixel of the image pick-up sensor 46. The offset processing removes a dark current component from the image signal after the defect correction processing and sets an accurate zero level. The gain correction processing adjusts the signal level by multiplying the image signal after the offset processing, by a specific gain.

The linear matrix processing increases the color reproducibility of the image signal after the gain correction processing. The gamma conversion processing adjusts the brightness and color saturation of the image signal after the linear matrix processing. By performing demosaicing processing (also referred to as isotropy processing) on the image signal after the gamma conversion processing, a signal of an insufficient color of each pixel is generated through interpolation. With the demosaicing processing, all pixels have signals of the respective colors of RGB.

The noise reduction unit 56 performs noise reduction processing by, for example, a moving average method or a median filter method, on the image signal after the demosaicing processing by the DSP 54 to reduce noise. The image signal after the noise reduction is stored in the memory 58.

The image processing unit 60 acquires the image signal from the memory 58, performs predetermined image processing on the acquired image signal, and generates a display image in which the observation object is captured. The content of image processing that is performed by the image processing unit 60 varies on an observation mode basis. The image processing unit 60 corresponds to an "image generation unit" of the present invention.

In the normal observation mode, the image processing unit 60 performs image processing, such as color conversion processing, chromatic emphasis processing, and structure emphasis processing, and generates a normal observation image. The color conversion processing is processing for performing color conversion on the image signal through 3×3 matrix processing, gradation transformation processing, and three-dimensional look-up table (LUT) processing. The chromatic emphasis processing is performed on the image signal after the color conversion processing. The structure emphasis processing is processing for emphasizing a specific tissue or structure included in an observation object, such as a blood vessel or a gland duct, and is performed on the image signal after the chromatic emphasis processing. In the special observation mode, the image processing unit 60 performs the above-described various image processing for emphasizing the blood vessel and hence generates a special observation image. In the special observation mode, the emission light quantity of the V-LED 30a is large. Thus, in the special observation image, a surface layer blood vessel is emphasized.

In the suitable object observation mode, the image processing unit 60 performs the above-described various image processing for emphasizing the structure suitable for the diagnosis purpose and hence generates a suitable object observation image. Image processing that is performed by the image processing unit 60 in the suitable object observation mode is described later in detail.

The display control unit 62 causes the display unit 18 to display the display image generated by the image processing unit 60. Thus, the normal observation image is displayed in the normal observation mode, the special observation image is displayed in the special observation mode, and the suitable object observation image is displayed in the suitable object observation mode.

The diagnosis purpose acquisition unit 64 acquires a diagnosis purpose from an endoscope information management system 72 connected to the diagnosis purpose acquisition unit 64 so as to communicate with each other through a network such as a local area network (LAN) via the data transmission/reception unit 66. The endoscope information management system 72 is a file server of a system such as a picture archiving and communication system (PACS) that files endoscope images. The endoscope information management system 72 has a data storage unit 74 that stores, as endoscope information management data, inspection information including a diagnosis purpose input from an input terminal (not illustrated), patient information, and so forth. The diagnosis purpose acquisition unit 64 receives the endoscope information management data from the data storage unit 74, and acquires the diagnosis purpose by extracting the diagnosis purpose from the endoscope information management data.

Next, image processing that is performed by the image processing unit 60 in the suitable object observation mode is described in detail.

Figure 5:
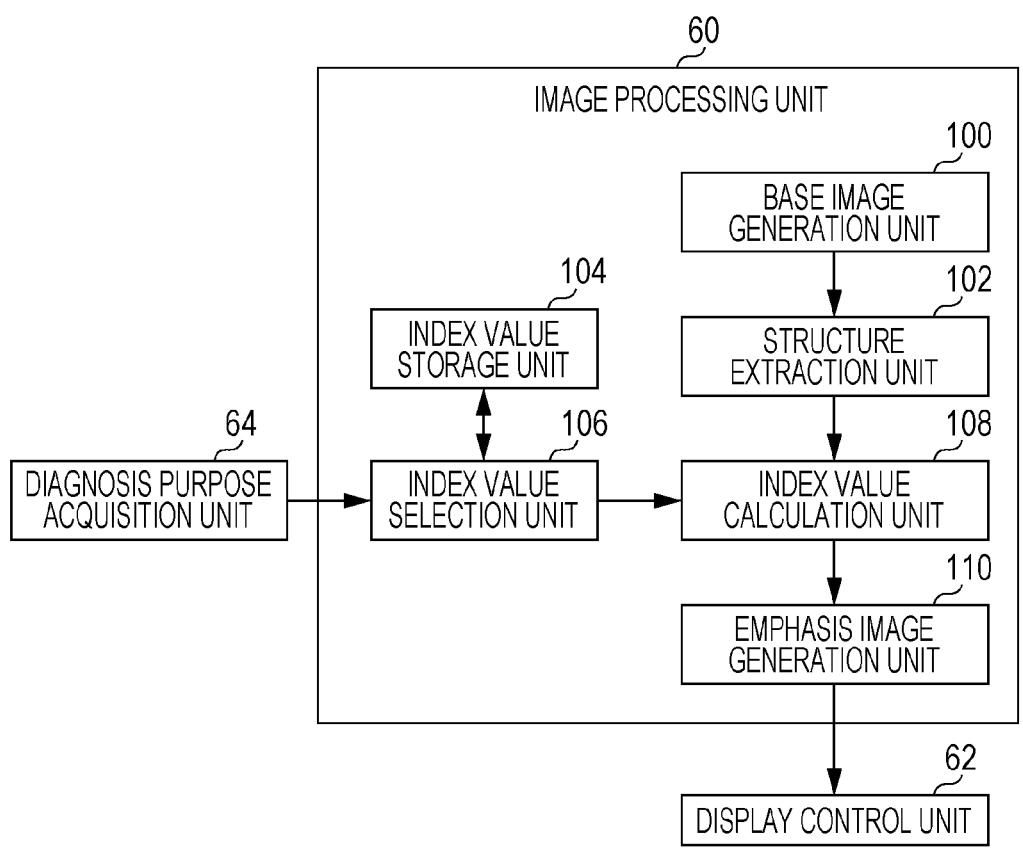
FIG. 5 is a block diagram explaining an image processing unit.

As illustrated in FIG. 5, the image processing unit 60 has a base image generation unit 100, a structure extraction unit 102, an index value storage unit 104, an index value selection unit 106, an index value calculation unit 108, and an emphasis image generation unit 110. The index value storage unit 104 is composed of a recording medium, such as a hard disc drive (HDD) or a solid state drive (SSD).

The base image generation unit 100 generates a base image, in which a structure of the observation object is expressed using a difference in color, from the image signal acquired from the memory 58, and acquires the generated base image as an endoscope image. That is, the base image generation unit 100 acquires an endoscope image obtained by an endoscope image-capturing an observation object. The base image is expressed with a hue corresponding to the set light quantity ratio, and the hue is slightly different from that of a normal observation image. An example of the base image may be an image with a color balance that a white plate in an image obtained by imaging with the set light quantity ratio appears white; a gray image obtained by assigning an image signal to one of an R channel, a G channel, and a B channel of the display unit 18 (for example, when the light quantity of the green light LG is large in a light quantity ratio of illumination light; an image signal is assigned to the G channel); an image with a pseudo color obtained by changing the gradation balance of an image signal and assigning the image signal to one of the channels; and other images. The base image generation unit 100 corresponds to an image acquisition unit of the present invention.

The structure extraction unit 102 generates a structure extraction image by extracting the structure of the observation object from the base image. For example, when the light source device 14 illuminates the observation object with illumination lights in different wavelength ranges, the structure extraction unit 102 extracts a blood vessel by taking a difference between images obtained by imaging the observation object illuminated with the respective illumination lights. To be specific, by taking a difference between an image obtained by imaging the observation object illuminated with the violet light LV and an image obtained by imaging the observation object illuminated with the blue light LB, a surface layer blood vessel or a blood vessel located at a shallower position than the position of the surface layer blood vessel can be extracted. In addition to or instead of extracting the blood vessel as described above, a structure of a gland duct may be extracted. The method of extracting a structure is not limited to the above-described method. In addition, while the structure extraction unit 102 extracts a blood vessel and a gland duct from the entirety of a base image in this embodiment, when a region of interest is designated by an operation with the instruction input part 19, a blood vessel and a gland duct may be extracted within only the designated region of interest.

The index value storage unit 104 stores correspondence between the diagnosis purpose and a plurality of index values relating to a structure of an observation object.

Diagnosis purposes include a first diagnosis purpose including screening and close inspection, a second diagnosis purpose relating to the type of disease, and a third diagnosis purpose relating to the stage of disease. The first diagnosis purpose is not limited to the above-described screening and close inspection, and there are a variety of diagnosis purposes. For example, the first diagnosis purpose includes treatment, post-treatment surveillance, and so forth. The types of index values are, for example, the density of a blood vessel, the uniformity of the thickness of a blood vessel, the complexity of a blood vessel, and the uniformity of a surface structure. The types of index values are not limited to the above-described example.

The density of a blood vessel is the proportion of a blood vessel per unit area. The uniformity of the thickness of a blood vessel is an index value relating to a variation in the thickness of a blood vessel. The complexity of a blood vessel is an index value indicating the degree of complexity of the shape of a blood vessel. For example, the complexity of a blood vessel is a value calculated by combining the number of branch points of an extracted blood vessel (branch number), the degree of meandering of the blood vessel, the degree of curve of the extracted blood vessel (curvature), and so forth. The uniformity of a surface structure is an index value relating to a variation in the shape of a gland duct.

As illustrated in FIG. 6, the index value storage unit 104 has first to third index value selection tables 104a to 104c. The first index value selection table 104a stores a first diagnosis purpose and an index value that is used for the first diagnosis purpose in an associated manner. For example, in the first index value selection table 104a, large intestine screening is associated with the complexity of a surface layer blood vessel and the complexity of a middle layer blood vessel; stomach screening is associated with the complexity of a middle layer blood vessel and the uniformity of a surface structure; and large intestine close inspection is associated with the density of a surface layer blood vessel.

The second index value selection table 104b stores a second diagnosis purpose and an index value that is used for the second diagnosis purpose in an associated manner. For example, in the second index value selection table 104b, Barrett's esophagus is associated with the density of a surface layer blood vessel, the complexity of a surface layer blood vessel, the density of a middle layer blood vessel, and the complexity of a middle layer blood vessel; large intestinal polyposis is associated with the uniformity of the thickness of a middle layer blood vessel and the uniformity of a surface structure; and angiodysplasia is associated with the density of a middle layer blood vessel.

The third index value selection table 104c stores a third diagnosis purpose and an index value that is used for the third diagnosis purpose in an associated manner. For example, in the third index value selection table 104c, the remission period of ulcerative colitis is associated with the complexity of a surface layer blood vessel and the complexity of a middle layer blood vessel; and the active period of ulcerative colitis is associated with the complexity of a surface layer blood vessel.

The correspondences stored in the first to third index value selection tables 104a to 104c can be appropriately updated, for example, through an input operation with the instruction input part 19. Moreover, new correspondences can be added to the first to third index value selection tables 104a to 104c.

The index value selection unit 106 acquires a diagnosis purpose from the diagnosis purpose acquisition unit 64, refers to the index value storage unit 104, and selects the index value that is used for the acquired diagnosis purpose. To be specific, the index value selection unit 106 refers to the first index value selection table 104*a* of the index value storage unit 104 when acquiring the first diagnosis purpose; refers to the second index value selection table 104*b* when acquiring the second diagnosis purpose; and refers to the third index value selection table 104*c* when acquiring the third diagnosis purpose. The index value selection unit 106 inputs the selected index value to the index value calculation unit 108.

In this embodiment, when a single diagnosis purpose is associated with a plurality of index values in the index value storage unit 104, the index value selection unit 106 selects a single index value designated through an operation with the instruction input part 19 from among the plurality of index values. For example, as illustrated in FIG. 7, when the acquired second diagnosis purpose is Barrett's esophagus and the complexity of a middle layer blood vessel is designated with the instruction input part 19, the index value selection unit 106 selects the designated complexity of a middle layer blood vessel, and inputs the selected complexity of a middle layer blood vessel to the index value calculation unit 108.

The index value calculation unit 108 uses the structure extraction image and calculates the selected index value. The index value calculation unit 108 calculates an index value for each pixel of the structure extraction image. For example, the index value calculation unit 108 calculates an index value of a single pixel by using data of pixels within a predetermined range including the pixels for which the index value is to be calculated (for example, a range of 99×99 pixels around the pixels for which the index value is to be calculated).

When a region of interest is set in part of the structure extraction image through an operation with the instruction input part 19, the index value calculation unit 108 calculates an index value within the set region of interest. When a region of interest is not set or when a region of interest is set for the entirety of the structure extraction image, the index value calculation unit 108 calculates an index value for the entirety of the structure extraction image.

While the index value calculation unit 108 calculates an index value by using a structure extraction image in this embodiment, the index value calculation unit 108 may calculate an index value by using an endoscope image acquired by the base image generation unit 100 serving as the image acquisition unit. For example, when a structure of an observation object clearly appears in an endoscope image, an index value can be calculated by using this endoscope image.

The emphasis image generation unit 110 uses the generated base image and the calculated index value, and generates a suitable object observation image serving as a first emphasis image. The emphasis image generation unit 110 generates a suitable object observation image, for example, by performing overlap processing of overlaying information based on the index value, on the base image. The overlap processing may be coloring processing corresponding to the index value. In the suitable object observation image after the coloring processing, a region with an index value that is a certain value or larger is displayed with a pseudo color. Hence, a structure suitable for a diagnosis purpose is emphasized. The emphasis image generation unit 110 corresponds to a first emphasis image generation unit of the present invention.

Figure 8:
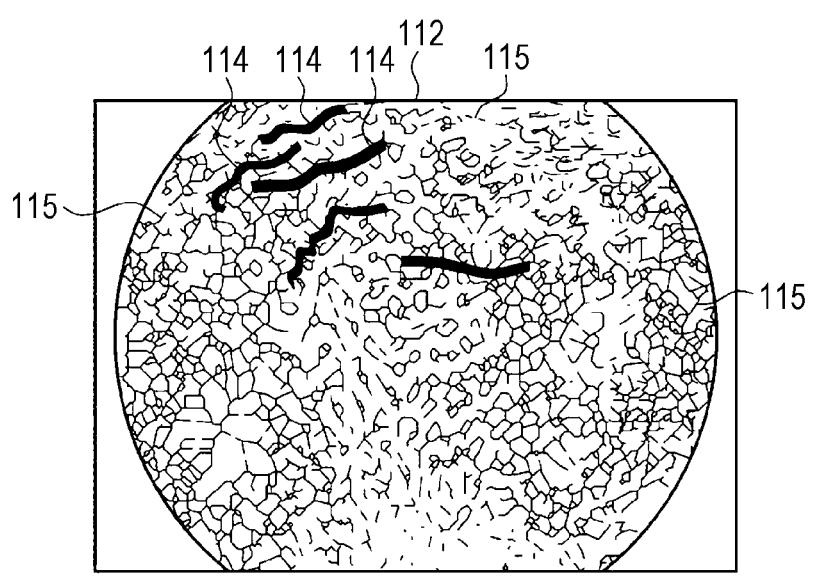
FIG. 8 illustrates a suitable object observation image displayed in an emphasized manner by using an index value.

For example, in a suitable object observation image 112 illustrated in FIG. 8, a region 114 having a complexity of a middle layer blood vessel being a certain value or larger is displayed with a pseudo color. The region 114 has, for example, a red-based color. In the suitable object observation image 112, although a surface layer blood vessel 115 is distributed in the entire screen, since the region 114 is displayed in an emphasized manner, the complexity of a middle layer blood vessel is easily recognized. Thus, a structure suitable for the diagnosis purpose can be further emphasized. In this case, information indicating the value of the index value may be overlaid on the base image.

Figure 9:
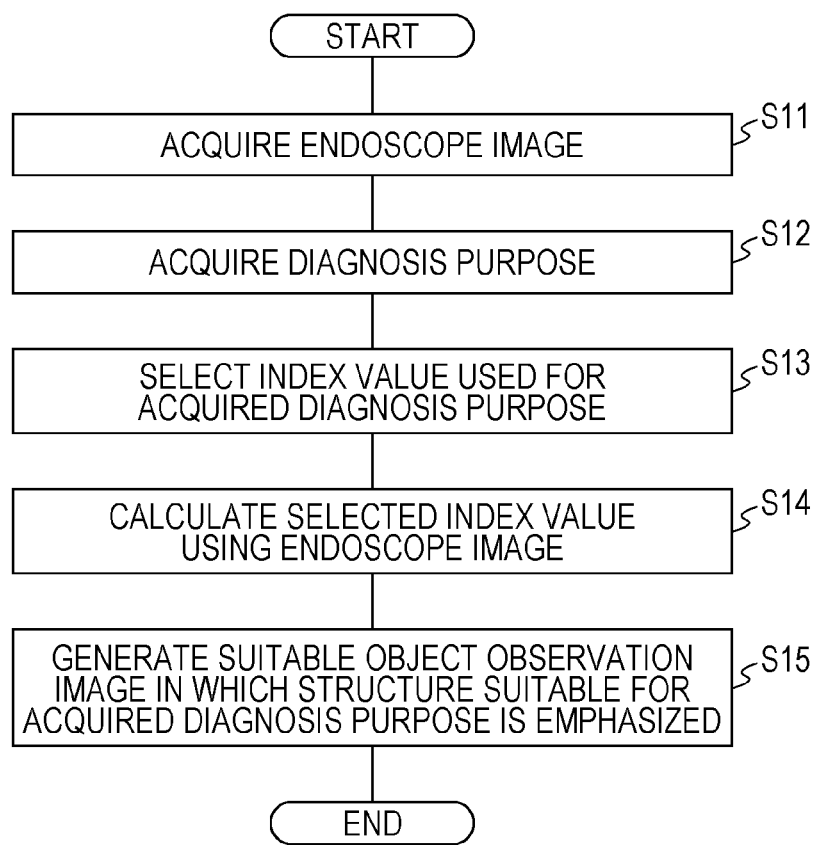
FIG. 9 is a flowchart explaining an operation in a suitable object observation mode of the endoscope system.

Next, an operation of the suitable object observation mode is described with reference to a flowchart in FIG. 9.

In the suitable object observation mode, illumination light including the violet light LV and the blue light LB is emitted, and an observation object illuminated with the illumination light is image-captured by the image pick-up sensor 46. The base image generation unit 100 generates a base image from an image signal output from the image pick-up sensor 46, and acquires the generated base image as an endoscope image (S11). The structure extraction unit 102 generates a structure extraction image by extracting a structure of the observation object from the base image.

The diagnosis purpose acquisition unit 64 acquires a diagnosis purpose from the data storage unit 74 of the endoscope information management system 72 through the network (S12). The diagnosis purpose acquisition unit 64 inputs the acquired diagnosis purpose to the index value selection unit 106 of the image processing unit 60.

The index value selection unit 106 refers to the index value storage unit 104 and selects the index value that is used for the acquired diagnosis purpose (S13). The index value storage unit 104 stores correspondence between the diagnosis purpose and a plurality of index values relating to a structure of an observation object. To be specific, the index value storage unit 104 has the first index value selection table 104*a* storing the index value that is used for the first diagnosis purpose; the second index value selection table 104*b* storing the index value that is used for the second diagnosis purpose; and the third index value selection table 104*c* storing the index value that is used for the third diagnosis purpose The index value selection unit 106 selects the index value from the first index value selection table 104*a* when the acquired diagnosis purpose is the first diagnosis purpose; selects the index value from the second index value selection table 104*b* when the acquired diagnosis purpose is the second diagnosis purpose; and selects the index value from the third index value selection table 104*c* when the acquired diagnosis purpose is the third diagnosis purpose. The index value selection unit 106 inputs the selected index value to the index value calculation unit 108.

The index value calculation unit 108 calculates the index value selected by the index value selection unit 106 from the structure extraction image (S14). When a structure of an observation object clearly appears in an endoscope image acquired by the base image generation unit 100 serving as an image acquisition unit, the index value calculation unit 108 can calculate an index value by using this endoscope image.

The emphasis image generation unit 110 uses the base image generated by the base image generation unit 100 and the index value calculated by the index value calculation unit 108, and generates a suitable object observation image (S15). The suitable object observation image is colored in accordance with the calculated index value, and the structure suitable for the diagnosis purpose is further emphasized. Then, the display unit 18 displays the suitable object observation image.

Since the diagnosis purpose acquisition unit 64 acquires a diagnosis purpose and the index value selection unit 106 selects the index value with which a structure suitable for the diagnosis purpose can be observed in this way, an index value can be calculated in accordance with the diagnosis purpose.

In the above-described first embodiment, the index value selection unit 106 selects a single index value for a single diagnosis purpose; however, a plurality of index values may be selected. In this case, the emphasis image generation unit 110 preferably performs coloring processing that is different depending on the selected index value.

Figure 10:
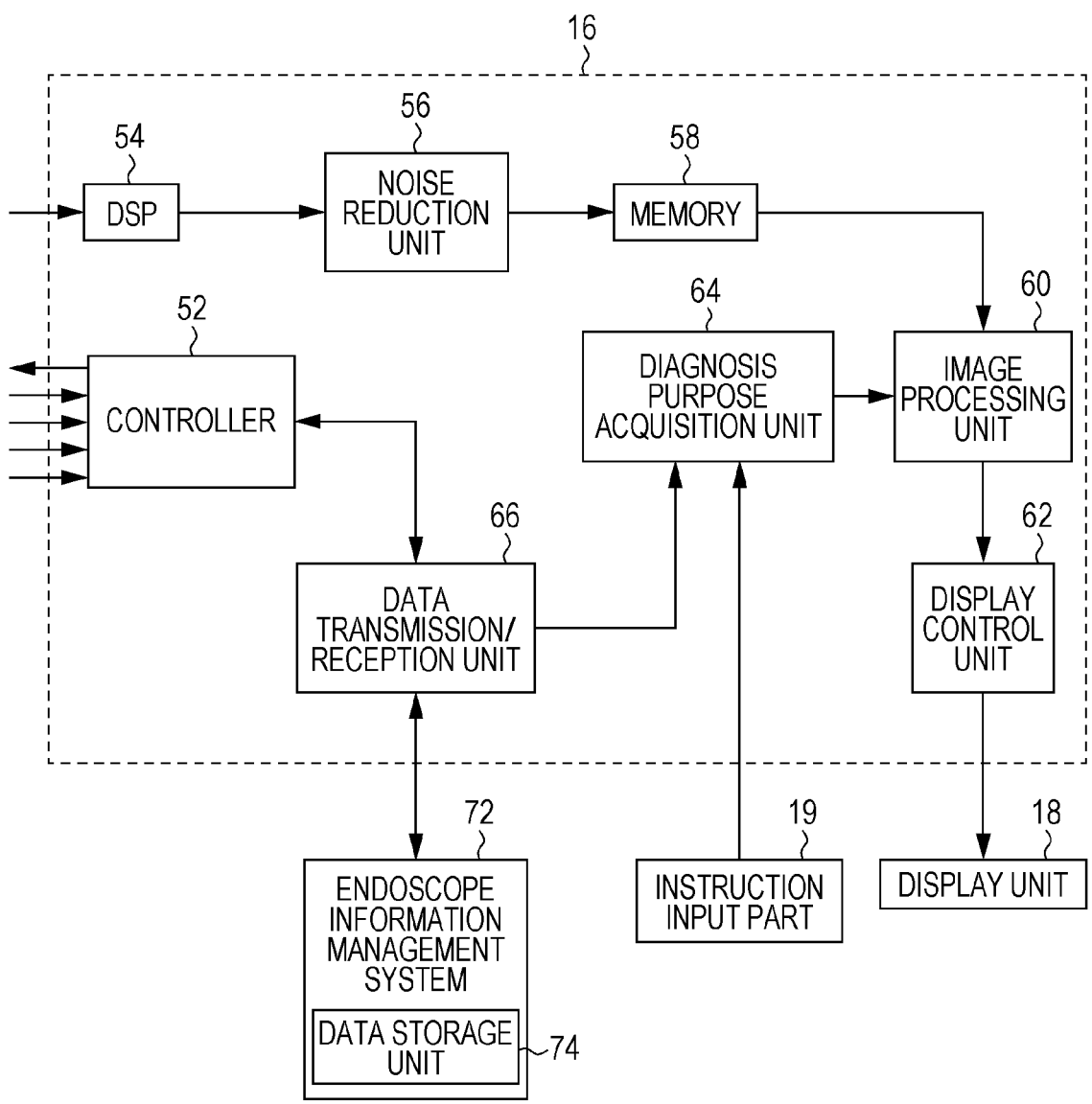
FIG. 10 is an illustration explaining acquisition of a diagnosis purpose from an instruction input part.

While the diagnosis purpose acquisition unit 64 acquires the diagnosis purpose from the endoscope information management system 72 through the network in the above-described first embodiment, as illustrated in FIG. 10, the diagnosis purpose acquisition unit 64 may acquire a diagnosis purpose input from the instruction input part 19 serving as a diagnosis purpose input unit, in addition to acquiring the diagnosis purpose from the endoscope information management system 72. In this case, the index value selection unit 106 uses the diagnosis purpose input from the instruction input part 19 with higher priority and selects the index value. Thus, during a diagnosis, the diagnosis purpose can be switched to a diagnosis purpose that is different from the diagnosis purpose acquired from the endoscope information management system 72, and the inspection can be continued.

Alternatively, the diagnosis purpose acquisition unit 64 may acquire the diagnosis purpose input from the instruction input part 19 instead of acquiring the diagnosis purpose from the endoscope information management system 72. In this case, the diagnosis purpose can be acquired even when the diagnosis purpose acquisition unit 64 is not connected to the endoscope information management system 72 through the network.

While a still image and/or a movie is stored in a storage (not illustrated) when the image storage operation unit 26 is operated in the above-described first embodiment, the processor device 16 may be provided with an image storage unit 116 (see FIG. 11) as a first image storage unit, and a suitable object observation image generated by the emphasis image generation unit 110 may be stored in association with at least one of the diagnosis purpose acquired by the diagnosis purpose acquisition unit 64 or the index value calculated by the index value calculation unit 108. A case where a suitable object observation image, a diagnosis purpose, and an index value are stored in an associated manner in the image storage unit 116 is described below.

Figure 11:
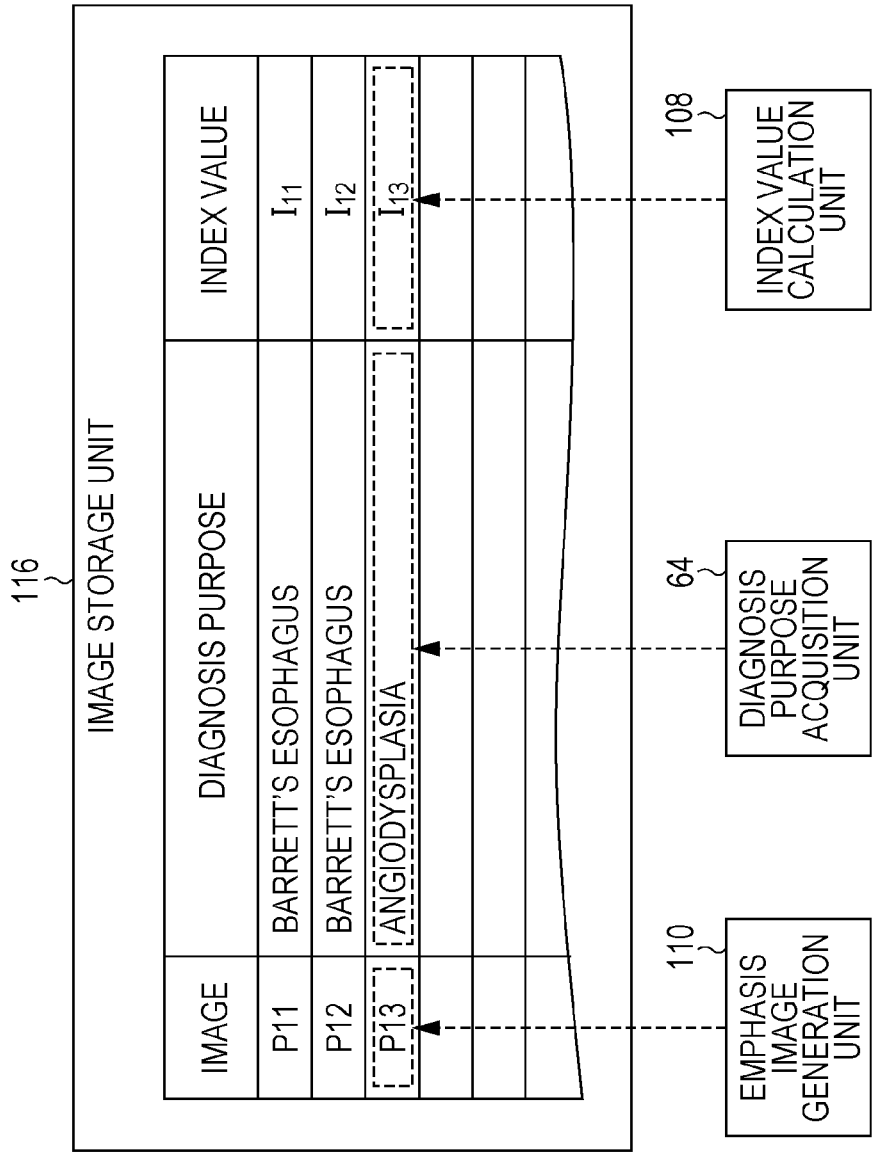
FIG. 11 is an illustration explaining an image storage unit.

For example, when the second diagnosis purpose acquired by the diagnosis purpose acquisition unit 64 is angiodysplasia, the index value selection unit 106 selects the density of a middle layer blood vessel as an index value, and the emphasis image generation unit 110 generates a suitable object observation image. When the image storage operating unit 26 is operated, as illustrated in FIG. 11, the image storage unit 116 stores the suitable object observation image generated by the emphasis image generation unit 110 as an image "P13" for storage, in a manner associated with the diagnosis purpose "angiodysplasia" acquired by the diagnosis purpose acquisition unit 64, and the density of a middle layer blood vessel "$I_{13}$" calculated by the index value calculation unit 108.

The image, the diagnosis purpose, and the index value stored in the image storage unit 116 can be displayed on the display unit 18. Accordingly, for a case of disease similar to the acquired diagnosis purpose, an image and a index value can be displayed by search from the image storage unit 116 through an operation with the instruction input part 19. Moreover, an image and a diagnosis purpose can be searched on the basis of the selected index value.

Furthermore, when the image storage unit 116 is connected to the endoscope information management system 72 so as to mutually communicated with each other through the network, data stored in the image storage unit 116 is transmitted to and stored in the data storage unit 74, and hence data can be shared with an endoscope system different from the endoscope system 10.

Second Embodiment

In the above-described first embodiment, the emphasis image generation unit 110 provides the emphasis display using the index value. In contrast, in a second embodiment, a structure parameter is calculated by using an index value, and emphasis display using the structure parameter is provided. In the second embodiment, an image processing unit 120 (see FIG. 12) is included instead of the image processing unit 60 of the first embodiment.

Figure 12:
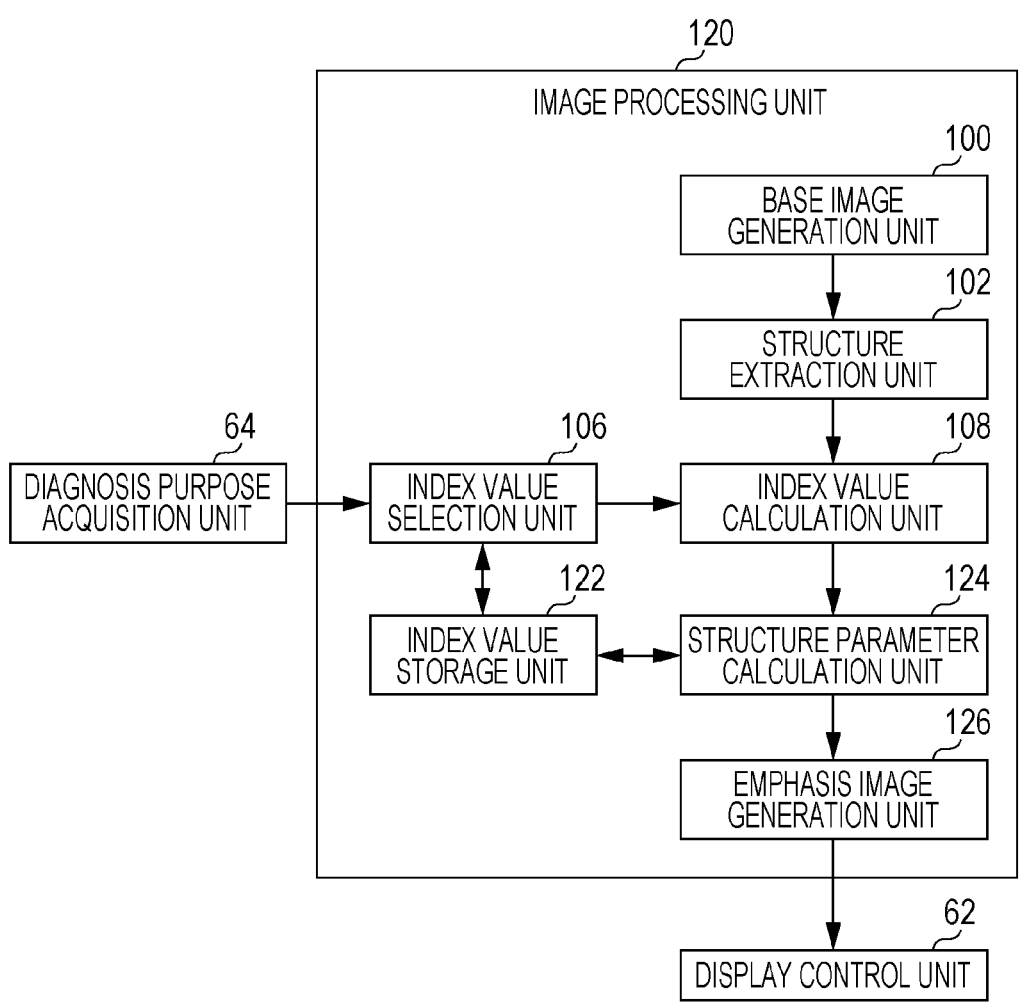
FIG. 12 is a block diagram explaining an image processing unit according to a second embodiment.

As illustrated in FIG. 12, the image processing unit 120 has an index value storage unit 122 instead of the index value storage unit 104 of the first embodiment, and has an emphasis image generation unit 126 instead of the emphasis image generation unit 110. The image processing unit 120 has, in addition to the respective units of the image processing unit 60 of the first embodiment, a structure parameter calculation unit 124.

The index value storage unit 122 stores, in addition to the index value and the diagnosis purpose, a weighting coefficient that is used by the structure parameter calculation unit 124 (described later) in an associated manner.

As illustrated in FIG. 13, the index value storage unit 122 has first to third index value selection tables 122a to 122c. Regarding the first to third index value selection tables 122a to 122c, the relationship between the diagnosis purpose and the index value is the same as that of the index value storage unit 104 of the first embodiment, and hence the description thereof is omitted. The relationship with the weighting coefficient (hereinafter, referred to as coefficient) is described below.

The first index value selection table 122a stores a first diagnosis purpose, an index value that is used for the first diagnosis purpose, and a coefficient per index value in an associated manner. For example, regarding large intestine screening, the coefficient for the complexity of a surface layer blood vessel is 0.5, and the coefficient for the complexity of a middle layer blood vessel is 1. Regarding stomach screening, the coefficient for the complexity of a middle layer blood vessel is 1, and the coefficient for the uniformity of a surface structure is 1. Regarding large intestine close inspection, the coefficient for the density of a surface layer blood vessel is 1.

The second index value selection table 122b stores a second diagnosis purpose, an index value that is used for the second diagnosis purpose, and a coefficient per index value in an associated manner. For example, regarding Barrett's esophagus, the coefficient for the density of a surface layer blood vessel, the coefficient for the complexity of a surface layer blood vessel, the coefficient for the density of a middle layer blood vessel, and the coefficient for the complexity of a middle layer blood vessel each are 1. Regarding large intestinal polyposis, the coefficient for the uniformity of the thickness of a middle layer blood vessel is 1, and the coefficient for the uniformity of a surface structure is 0.5. Regarding angiodysplasia, the coefficient for the density of a middle layer blood vessel is 1.

The third index value selection table 122c stores a third diagnosis purpose, an index value that is used for the third diagnosis purpose, and a coefficient per index value in an associated manner. For example, regarding the remission period of ulcerative colitis, the coefficient for the complexity of a surface layer blood vessel and the coefficient for the complexity of a middle layer blood vessel each are 1. Regarding the active period of ulcerative colitis, the coefficient for the complexity of a surface layer blood vessel is 1.

The correspondences stored in the first to third index value selection tables 122a to 122c can be appropriately updated, for example, through an input operation with the instruction input part 19. Moreover, new correspondences can be added to the first to third index value selection tables 122a to 122c.

In this embodiment, the diagnosis purpose acquisition unit 64 acquires one of the first to third diagnosis purposes. However, the diagnosis purpose acquisition unit 64 may acquire a composite purpose in which a plurality of diagnosis purposes such as the first diagnosis purpose and the second diagnosis purpose are combined. To prepare for such a case, the index value storage unit 122 may be provided with a table for a composite purpose. The table for a composite purpose stores a composite purpose, index values that are used for the composite purpose, and a coefficient per index value in an associated manner. The index values that are used for the composite purpose are index values that are used for respective diagnosis purposes constituting the composite purpose. The coefficient stored in the table for a composite purpose is set, for example, to a larger value for index values that overlap one another by a larger number among the index values that are used for the respective diagnosis purposes constituting the composite purpose.

The structure parameter calculation unit 124 calculates a structure parameter by using the index value calculated by the index value calculation unit 108. To be specific, the structure parameter calculation unit 124 calculates a structure parameter by weighting a plurality of index values with a coefficient (weighting coefficient) determined in accordance with the diagnosis purpose and arithmetically operating the index values. The structure parameter calculation unit 124, when calculating the structure parameter, refers to the index value storage unit 122 and uses the coefficient associated with the index value calculated by the index value calculation unit 108.

The structure parameter is a numerical value that is calculated by using index values in such a way of imitating the viewpoint of a doctor who carries out a diagnosis with regard to the entirety of the index values. For example, the structure parameter is calculated through arithmetic operation such as addition of index values having mutually different dimensions (units), and hence the structure parameter has no physical meaning; however, the structure parameter functions as an index of a diagnosis. That is, the structure parameter differs from the index value in that the structure parameter has no physical meaning.

For example, when the second diagnosis purpose acquired by the diagnosis purpose acquisition unit 64 is Barrett's esophagus, the structure parameter calculation unit 124 calculates a structure parameter by multiplying each of the density of a surface layer blood vessel, the complexity of a surface layer blood vessel, the density of a middle layer blood vessel, and the complexity of a middle layer blood vessel by 1 and adding these values. While the structure parameter calculation unit 124 calculates a single structure parameter by using a plurality of index values in this embodiment, it is not limited thereto, and the structure parameter calculation unit 124 may calculate two or more structure parameters. The structure parameter may be calculated by any method. For example, without being limited to the calculation of the structure parameter using the weighted sum of the plurality of index values as described above, a structure parameter may be calculated through arithmetic operation involving mixture of at least two of addition, subtraction, multiplication, and division, or a structure parameter may be calculated by using any of other functions. Further, the structure parameter calculation unit 124 may calculate a structure parameter by multiplying a single index value by a weighting coefficient.

The emphasis image generation unit 126 uses the generated base image and the calculated structure parameter, and generates a suitable object observation image as a second emphasis image. The emphasis image generation unit 126 generates a suitable object observation image, for example, by performing overlap processing of overlaying information based on the structure parameter, on the base image. The emphasis image generation unit 126 corresponds to a second emphasis image generation unit of the present invention.

Figure 14:
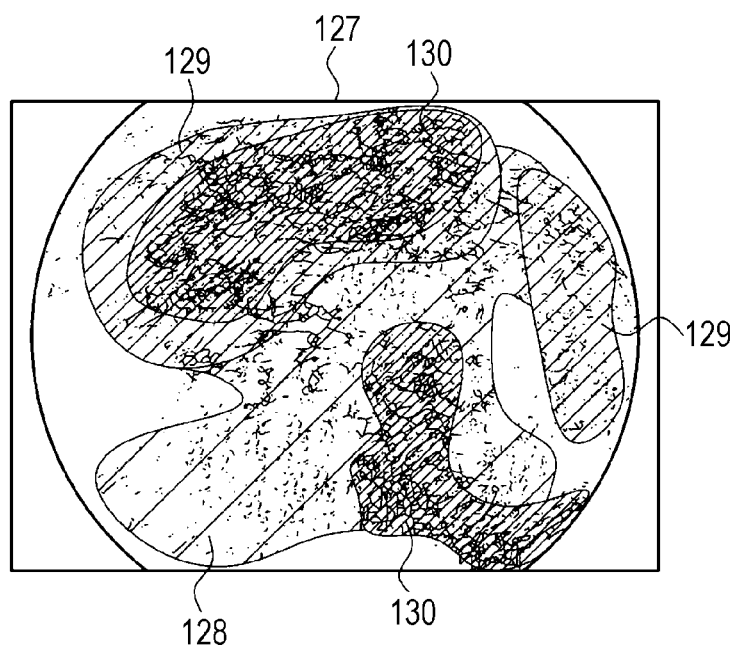
FIG. 14 illustrates a suitable object observation image displayed in an emphasized manner by using a structure parameter.

For example, in a suitable object observation image 127 illustrated in FIG. 14, regions 128 to 130 are displayed with different colors in accordance with the structure parameters. For example, the region 128 among the regions 128 to 130 has the smallest structure parameter and hence has a blue-based color. The region 129 has a larger structure parameter than the region 128 and hence has a yellow-based color. The region 130 has a larger structure parameter than the region 129 and hence has a red-based color. In this case, information indicating the value of the structure parameter may be overlaid on the base image. Thus, a structure suitable for the diagnosis purpose can be further emphasized.

In the above-described second embodiment, the processor device 16 may be provided with an image storage unit 132 (see FIG. 15) as a second image storage unit, and a suitable object observation image generated by the emphasis image generation unit 126 may be stored in association with at least one of the diagnosis purpose acquired by the diagnosis purpose acquisition unit 64 or the structure parameter calculated by the structure parameter calculation unit 124. Hereinafter, a case where, in addition to the diagnosis purpose and the structure parameter, the index value calculated by the index value calculation unit 108 is associated with the suitable object observation image and stored is described.

Figure 15:
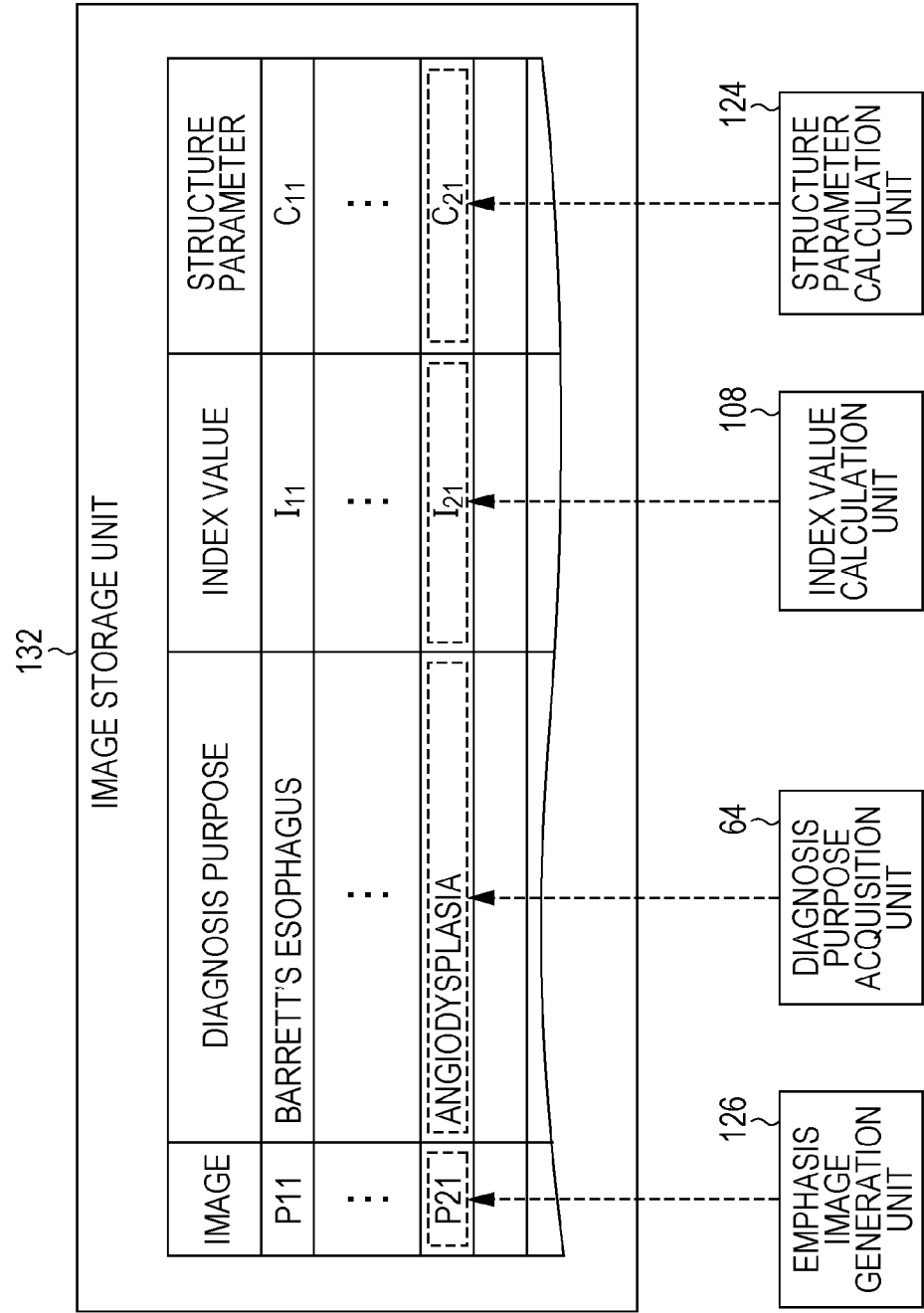
FIG. 15 is an illustration explaining an image storage unit according to the second embodiment.

For example, when the second diagnosis purpose acquired by the diagnosis purpose acquisition unit 64 is angiodysplasia, the index value selection unit 106 selects the density of a middle layer blood vessel as an index value, and the emphasis image generation unit 126 generates a suitable object observation image. When the image storage operating unit 26 is operated, as illustrated in FIG. 15, the image storage unit 132 stores the suitable object observation image generated by the emphasis image generation unit 126 as an image "P21" for storage, in a manner associated with the diagnosis purpose "angiodysplasia" acquired by the diagnosis purpose acquisition unit 64, the density of a middle layer blood vessel "$I_{21}$" calculated by the index value calculation unit 108, and a structure parameter "$C_{21}$" calculated by the structure parameter calculation unit 124.

Third Embodiment

In the above-described second embodiment, the emphasis image generation unit 126 provides the emphasis display using the structure parameter. In contrast, in a third embodiment, the state of a mucous membrane of an observation object is determined by using a structure parameter, and emphasis display using the determination result is provided. In the third embodiment, an image processing unit 140 (see FIG. 16) is included instead of the image processing unit 120 of the second embodiment.

Figure 16:
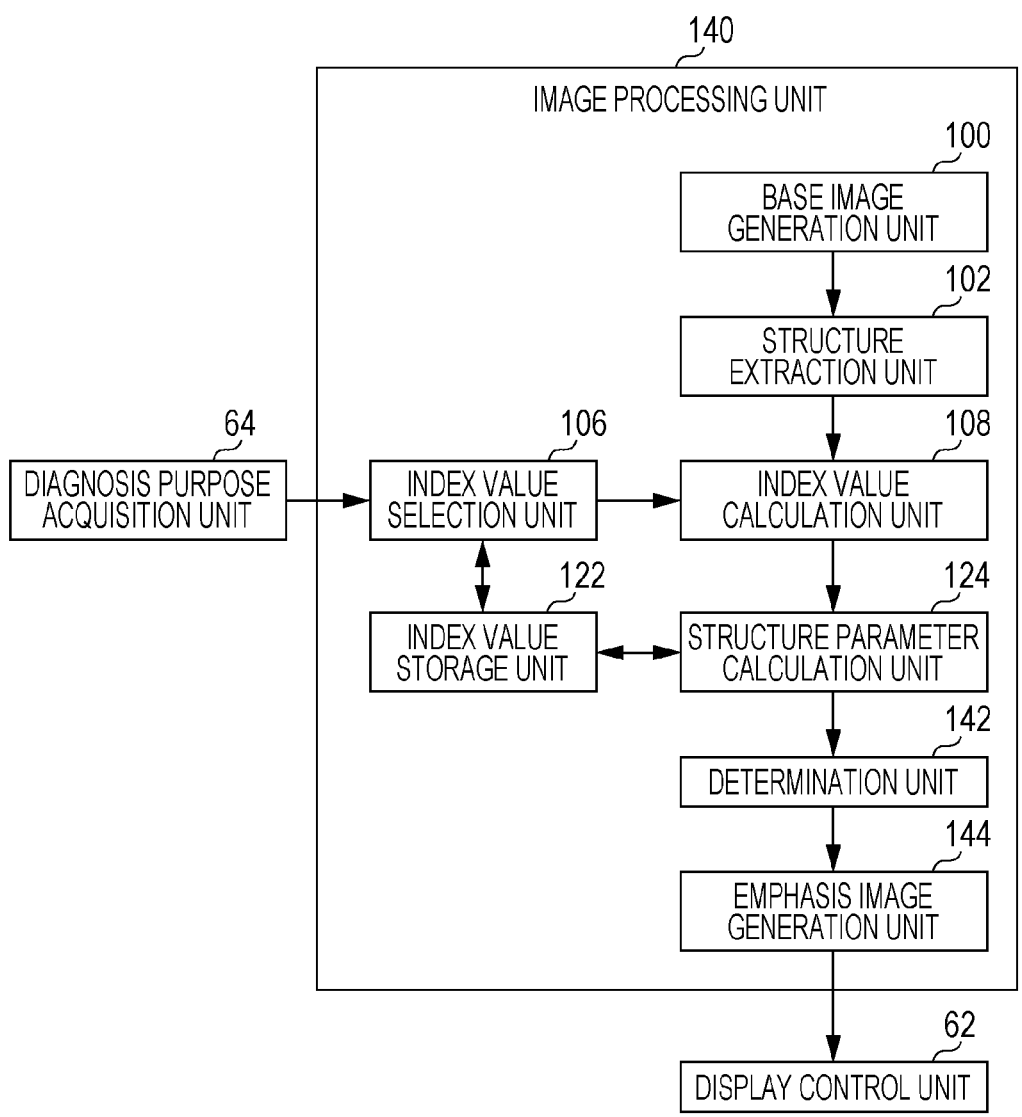
FIG. 16 is a block diagram explaining an image processing unit according to a third embodiment.

As illustrated in FIG. 16, the image processing unit 140 in this case further has a determination unit 142 in addition to the respective units of the image processing unit 120. The image processing unit 140 has an emphasis image generation unit 144 instead of the emphasis image generation unit 126 of the second embodiment.

The determination unit 142 determines the state of the mucous membrane of the observation object by using the structure parameter calculated by the structure parameter calculation unit 124. "The state of a mucous membrane" of an observation object is a comprehensive status of the entirety of a mucous membrane including a blood vessel and a gland duct, and is, for example, "normal", "adenoma (suspected adenoma)", "cancer (suspected cancer)", or other status. Thus, the determination unit 142 determines the state of the mucous membrane as being in one of three types of states of normal, adenoma, and cancer.

For example, it is assumed that a coefficient that is used for calculating a structure parameter is set to a balance that can determine one of the three types of states of normal, adenoma, and cancer. In this case, the determination unit 142 determines the state of a mucous membrane by comparing a numerical value of the structure parameter and a threshold value. To be specific, when the structure parameter is equal to or smaller than a first threshold value, the determination unit 142 determines that the state of the mucous membrane of the observation object is "normal". When the structure parameter is larger than the first threshold value and equal to or smaller than a second threshold value, the determination unit 142 determines that the state of the mucous membrane of the observation object is "adenoma". When the structure parameter is larger than the second threshold value, the determination unit 142 determines that the state of the mucous membrane of the observation object is "cancer".

The emphasis image generation unit 144 uses the generated base image and the determination result of the determination unit 142, and generates a suitable object observation image as a third emphasis image. The emphasis image generation unit 110 generates a suitable object observation image, for example, by performing overlap processing of overlaying information based on the determination result, on the base image. The emphasis image generation unit 144 corresponds to a third emphasis image generation unit of the present invention.

Figure 17:
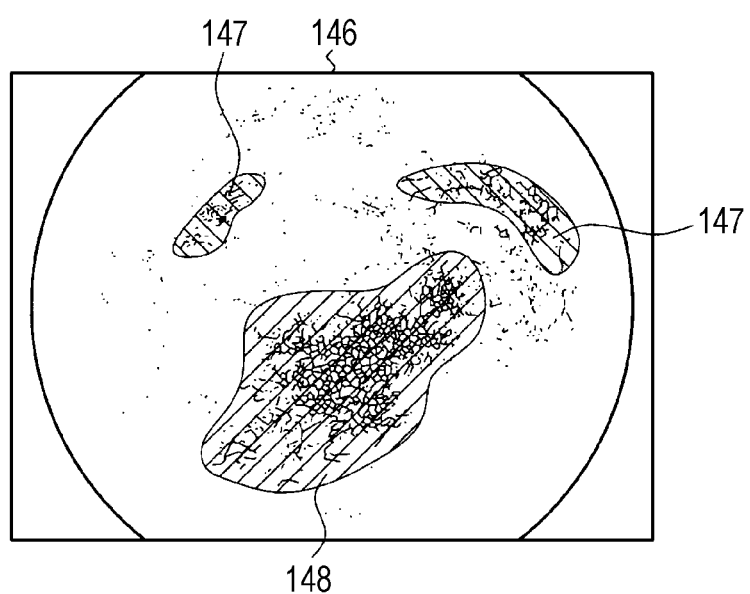
FIG. 17 illustrates a suitable object observation image displayed in an emphasized manner by using a determination result.

For example, in a suitable object observation image 146 illustrated in FIG. 17, a region 147 is a region that is determined as "adenoma". A region 148 is a region that is determined as "cancer". The region 147 and the region 148 are displayed with different colors. For example, the region 147 has a yellow-based color, and the region 148 has a red-based color. The region determined as "normal" is not colored in this embodiment; however, the region may be colored with, for example, a blue-based color. Information indicating the determination result may be displayed for the base image. By determining the state of a mucous membrane of an observation object using a structure parameter and displaying the determination result in this way, a diagnosis can be further directly assisted.

In the above-described third embodiment, the processor device 16 may be provided with an image storage unit 150 (see FIG. 18) as a third image storage unit, and a suitable object observation image generated by the emphasis image generation unit 144 may be stored in association with at least one of the diagnosis purpose acquired by the diagnosis purpose acquisition unit 64 or the determination result of the determination unit 142. Hereinafter, a case where, in addition to the diagnosis purpose and the determination result, the structure parameter is associated with the suitable object observation image and stored is described.

Figure 18:
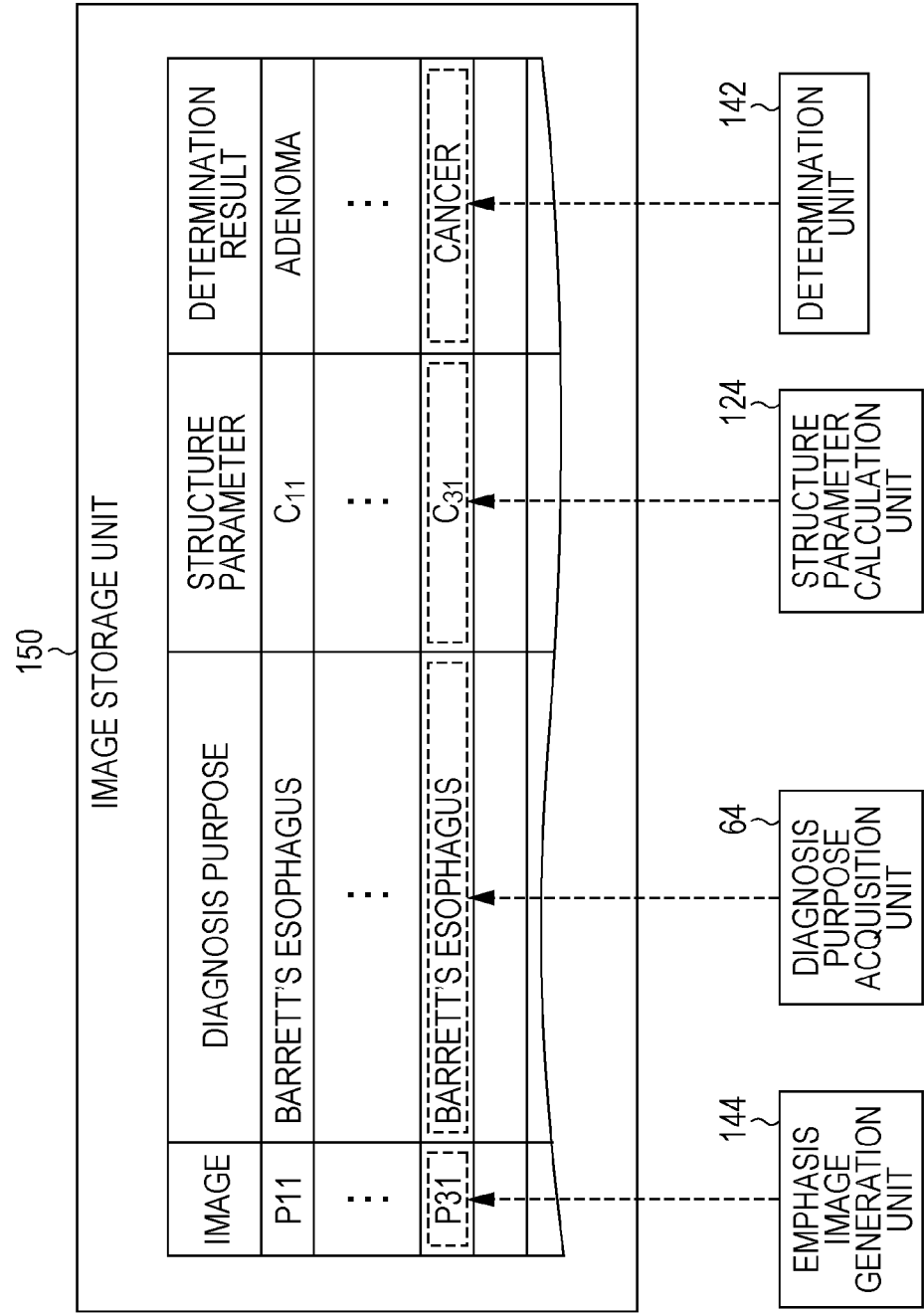
FIG. 18 is an illustration explaining an image storage unit according to the third embodiment.

For example, as illustrated in FIG. 18, the suitable object observation image generated by the emphasis image generation unit 126 when the second diagnosis purpose acquired by the diagnosis purpose acquisition unit 64 is Barrett's esophagus is stored as an image "P31" for storage in a manner associated with the diagnosis purpose "Barrett's esophagus" acquired by the diagnosis purpose acquisition unit 64, the structure parameter "$C_{31}$" calculated by the structure parameter calculation unit 124, and the determination result "cancer" of the determination unit 142.

REFERENCE SIGNS LIST 10 endoscope system
12 endoscope
12*a* insertion section
12*b* operation section
14 light source device
16 processor device
18 display unit
19 instruction input part
21 distal end portion
22 bending portion
23 flexible pipe portion
25 angle knob
26 image storage operating unit
27 mode switching unit
28 zoom operating unit
30 light source
30*a* V-LED
30*b* B-LED
30*c* G-LED
30*d* R-LED
30*e* optical filter
32 light source control unit
34 light guide
36 illumination optical system
38 image pick-up optical system
40 illumination lens
42 objective lens
44 zoom lens
46 image pick-up sensor
48 CDS/AGC circuit
50 A/D conversion circuit
52 controller
54 DSP
56 noise reduction unit
58 memory 60 image processing unit
62 display control unit
64 diagnosis purpose acquisition unit
66 data transmission/reception unit
72 endoscope information management system
74 data storage unit
100 base image generation unit
102 structure extraction unit
104 index value storage unit
104a first index value selection table
104b second index value selection table
104c third index value selection table
106 index value selection unit
108 index value calculation unit
110 emphasis image generation unit
112 suitable object observation image
114 region
115 surface layer blood vessel
116 image storage unit
120 image processing unit
122 index value storage unit
122a first index value selection table
122b second index value selection table
122c third index value selection table
124 structure parameter calculation unit
126 emphasis image generation unit
127 suitable object observation image
128 region
129 region
130 region
132 image storage unit
140 image processing unit
142 determination unit
144 emphasis image generation unit
146 suitable object observation image
147 region
148 region
150 image storage unit

What is claimed is:

1. A processor device comprising:
a memory; and
a processor, configured to:
   acquire an endoscope image obtained by an endoscope image-capturing an observation object;
   acquire a diagnosis purpose;
   select an index value that is used for the acquired diagnosis purpose according to correspondence between the diagnosis purposes and a plurality of index values relating to a structure of the observation object and stored in the memory, wherein the structure of the observation object comprises at least one of a structure of a blood vessel and a structure of a gland duct of the observation object; and
   calculate the selected index value according to the endoscope image.

2. The processor device according to claim 1,
wherein the diagnosis purpose includes a first diagnosis purpose including screening and close inspection, a second diagnosis purpose relating to a type of disease, and a third diagnosis purpose relating to a stage of disease, and
wherein the processor selects the index value in accordance with one diagnosis purpose of the first to third diagnosis purposes.

3. The processor device according to claim 1, wherein the processor is further configured to:
generate a first emphasis image in which the structure is emphasized according to the endoscope image and the calculated index value.

4. The processor device according to claim 2, wherein the processor is further configured to:
generate a first emphasis image in which the structure is emphasized according to the endoscope image and the calculated index value.

5. The processor according to claim 3, wherein the memory further stores the first emphasis image in association with at least one of the acquired diagnosis purpose or the calculated index value.

6. The processor according to claim 4, wherein the memory further stores the first emphasis image in association with at least one of the acquired diagnosis purpose or the calculated index value.

7. The processor device according to claim 1, wherein the processor is further configured to:
calculate a structure parameter of the structure by weighting a plurality of the index values with a weighting coefficient determined in accordance with the diagnosis purpose and arithmetically operating the index values.

8. The processor device according to claim 2, wherein the processor is further configured to:
calculate a structure parameter of the structure by weighting a plurality of the index values with a weighting coefficient determined in accordance with the diagnosis purpose and arithmetically operating the index values.

9. The processor device according to claim 3, wherein the processor is further configured to:
calculate a structure parameter of the structure by weighting a plurality of the index values with a weighting coefficient determined in accordance with the diagnosis purpose and arithmetically operating the index values.

10. The processor device according to claim 4, wherein the processor is further configured to:
calculate a structure parameter of the structure by weighting a plurality of the index values with a weighting coefficient determined in accordance with the diagnosis purpose and arithmetically operating the index values.

11. The processor device according to claim 7, wherein the processor is further configured to:
generate a second emphasis image in which the structure is emphasized according to the endoscope image and the calculated structure parameter.

12. The processor device according to claim 11, wherein the memory further stores the second emphasis image in association with at least one of the acquired diagnosis purpose or the calculated structure parameter.

13. The processor device according to claim 7, wherein the processor is further configured to:
determine a state of a mucous membrane of the observation object according to the structure parameter.

14. The processor device according to claim 11, wherein the processor is further configured to:
determine a state of a mucous membrane of the observation object according to the structure parameter.

15. The processor device according to claim 12, wherein the processor is further configured to:
determine a state of a mucous membrane of the observation object according to the structure parameter.

16. The processor device according to claim 13, wherein the processor is further configured to:
generate a third emphasis image in which the structure is emphasized according to the endoscope image and a result of the determination.

17. The processor device according to claim 16, wherein the memory further stores the third emphasis image in association with at least one of the acquired diagnosis purpose or the result of the determination.

18. The processor device according to claim 1,
wherein the processor device is connected to an endoscope information management system having a data memory that stores endoscope information management data including the diagnosis purpose so as to mutually communicate with each other through a network, and
wherein the processor receives the endoscope information management data through the network, and acquires the diagnosis purpose by extracting the diagnosis purpose from the received endoscope information management data.

19. The processor device according to claim 1, wherein the processor is further configured to:
acquire an input of the diagnosis purpose.

20. An endoscope system comprising:
a light source that emits illumination light;
a memory;
a processor, configured to:
acquire an endoscope image acquired by an endoscope image-capturing an observation object illuminated with the illumination light;
generate a structure extraction image obtained by extracting a structure of the observation object according to the endoscope image;
acquire a diagnosis purpose;
select an index value that is used for the acquired diagnosis purpose according to correspondence between the diagnosis purposes and a plurality of index values relating a structure of the observation object and stored in the memory;
calculate the selected index value according to the structure extraction image;
generate a first emphasis image in which the structure is emphasized according to the endoscope image and the calculated index value; and
a display that displays the first emphasis image.

* * * * *